(12) United States Patent
Furuta et al.

(10) Patent No.: US 10,921,281 B2
(45) Date of Patent: Feb. 16, 2021

(54) GAS SENSOR ELEMENT, GAS SENSOR, AND METHOD FOR PRODUCING GAS SENSOR ELEMENT

(71) Applicant: NGK Spark Plug Co., LTD., Nagoya (JP)

(72) Inventors: Hitoshi Furuta, Nagoya (JP); Tetsuo Yamada, Nagoya (JP); Akinori Kojima, Nagoya (JP)

(73) Assignee: NGK Spark Plug Co., LTD., Nagoya (JP)

( * ) Notice: Subject to any disclaimer, the term of this patent is extended or adjusted under 35 U.S.C. 154(b) by 26 days.

(21) Appl. No.: 16/279,786

(22) Filed: Feb. 19, 2019

(65) Prior Publication Data

US 2019/0257783 A1 Aug. 22, 2019

(30) Foreign Application Priority Data

Feb. 22, 2018 (JP) .................................. 2018-029867
Aug. 22, 2018 (JP) .................................. 2018-155442

(51) Int. Cl.
*G01N 27/407* (2006.01)
*G01N 27/41* (2006.01)
*G01N 27/409* (2006.01)
*G01N 33/00* (2006.01)

(52) U.S. Cl.
CPC ....... *G01N 27/4077* (2013.01); *G01N 27/409* (2013.01); *G01N 27/41* (2013.01); *G01N 33/0037* (2013.01)

(58) Field of Classification Search
CPC .......... G01N 27/4071; G01N 27/4077; G01N 27/4074
See application file for complete search history.

(56) References Cited

U.S. PATENT DOCUMENTS

| | | | | |
|---|---|---|---|---|
| 2013/0104625 | A1* | 5/2013 | Otsuka | G01N 33/0037 73/23.31 |
| 2015/0013431 | A1* | 1/2015 | Kakimoto | F01N 11/007 73/23.31 |
| 2016/0161445 | A1* | 6/2016 | Sakakibara | G01N 27/419 204/424 |

FOREIGN PATENT DOCUMENTS

JP 2016-080684 A 5/2016

\* cited by examiner

*Primary Examiner* — Alexander S Noguerola
(74) *Attorney, Agent, or Firm* — Leason Ellis LLP

(57) ABSTRACT

A gas sensor element configured to detect a first component and a second component of a measurement target gas comprises an element body portion, a first detection portion, a second detection portion with a porous region, and an element protection portion. The element protection portion covers the porous region and a region at the front side with respect to the porous region in a normal side face, and covers a part of a region at the front side with respect to the second detection portion without covering the second detection portion in a second detection side face. The element protection portion is formed so as not to cover the second detection portion but to cover the porous portion of the first detection portion.

9 Claims, 10 Drawing Sheets

INTERVAL DIMENSION D1 [mm]
(INTERVAL DIMENSION BETWEEN AMMONIA DETECTION PORTION AND SPECIFIC PROTECTION PORTION)

GAS SENSOR ELEMENT, GAS SENSOR, AND METHOD FOR PRODUCING GAS SENSOR ELEMENT

This application claims the benefit of Japanese Patent Applications No. 2018-029867, filed Feb. 22, 2018 and No. 2018-155442, filed Aug. 22, 2018, which are incorporated herein by reference in their entirety.

FIELD OF THE INVENTION

The present disclosure relates to a gas sensor element, a gas sensor, and a method for producing the gas sensor element.

BACKGROUND OF THE INVENTION

A gas sensor including a gas sensor element for detecting a specific gas contained in a measurement target gas is known.

Such a gas sensor is provided to an exhaust pipe of an internal combustion engine of an automobile or the like, for example, and is used in order to detect the concentration of a specific component (oxygen, NOx, or the like) in the exhaust gas of the internal combustion engine. Some of the gas sensor elements include: a cell including a solid electrolyte body and an electrode; and an insulation protection layer laminated to the cell. In some of the insulation protection layers, a porous portion for protecting the electrode of the cell is embedded in a part of the insulation protection layer.

Such a gas sensor element is configured such that the porous portion covers the electrode of the cell. The porous portion protects the electrode by suppressing a foreign object such as soot from directly coming into contact with the electrode, while allowing passage of gas between the outside of the gas sensor element and the electrode. See Japanese Unexamined Publication No. 2016-080684.

Problems to be Solved by the Invention

However, in the case of the gas sensor element described above, if the temperature decreases below the freezing point in a state where moisture is contained in the porous portion, the gas sensor element (in particular, the boundary between the insulation protection layer and the porous portion) could be broken (occurrence of crack, etc.) due to stress caused by change in the volume of the moisture.

That is, in a case where the gas sensor is installed in an environment having a large amount of moisture, moisture is contained in the porous portion, volume change of the moisture is caused by decrease of the temperature, and thus, the gas sensor element could be broken. For example, in an exhaust pipe of an internal combustion engine, in a low temperature environment such as in winter, condensed water easily accumulates while the internal combustion engine is stopped, and the condensed water reaches the gas sensor together with the exhaust gas when the internal combustion engine is started. This could cause moisture to be contained in the porous portion.

Therefore, objects of the present disclosure are: to provide a gas sensor element that includes an insulation protection layer having a porous portion, and that is less likely to be broken even when the gas sensor element is used in a low temperature environment; to provide a gas sensor that includes the gas sensor element; and to provide a method for producing the gas sensor element.

SUMMARY OF THE INVENTION

Means for Solving the Problems

One mode of the present disclosure is a gas sensor element configured to detect a first component and a second component in a measurement target gas. The gas sensor element includes an element body portion, a first detection portion, a second detection portion, and an element protection portion.

The element body portion extending in the axial direction, and has a front end face formed at the front end in the axial direction, a rear end face formed at the rear end in the axial direction, and a plurality of side faces extending from the front end face to the rear end face. The first detection portion pumps out or pumps in the measurement target gas through a porous portion formed at at least one of the plurality of side faces, and detects the first component. The second detection portion is provided at the rear side with respect to the front end of the porous portion, and detects the second component. The element protection portion is configured to cover at least the porous portion.

The plurality of side faces include a second detection side face on which the second detection portion is provided, and normal side faces which are not the second detection side face.

The element body portion comprises a second detection region that contains the second detection portion and extends in the axial direction, and a porous region that contains the porous portion and extends in the axial direction, the element protection portion covers the porous region and a region at the front side with respect to the porous region at the normal side faces, and covers at a part of a region at the front side with respect to the second detection portion except for the second detection portion at the second detection side.

That is, this gas sensor element includes the element protection portion that covers the porous portion and a front end region with respect to the porous portion. Since the element protection portion alleviates thermal shock caused by temperature decrease or temperature increase, occurrence of breakage in the porous portion or at the boundary of the porous portion can be suppressed. In addition, the element protection portion is formed so as to cover the porous portion of the first detection portion without covering the second detection portion. Accordingly, the measurement target gas that is to reach the second detection portion is not blocked by the element protection portion.

Thus, in the gas sensor element, the element protection portion alleviates thermal shock, and thus, occurrence of breakage of the gas sensor element can be suppressed. In addition, since the measurement target gas easily reaches the second detection portion, decrease of the detection accuracy at the second detection portion can be suppressed.

It should be noted that the porous portion is formed, at the plurality of side faces, in a front end region of two regions obtained by bisecting the element body portion in the axial direction.

Next, in the gas sensor element of the present disclosure, the element body portion may include a heater configured to heat the first detection portion and the second detection portion.

The heater includes a heat generation portion. The heat generation portion is disposed so as to overlap at least one of the second detection region and a first detection region formed adjacent to the second detection region in the axial direction.

The second detection portion includes a pair of detection electrodes. The pair of detection electrodes is disposed inside the arrangement region of the heat generation portion in the width direction of the element body portion.

When the pair of detection electrodes is configured as described above, the entirety of the pair of detection electrodes easily receives heat from the heat generation portion, compared with a case where the pair of detection electrodes is disposed in a region larger than the arrangement region of the heat generation portion.

Thus, in the gas sensor element, occurrence of unevenness of the temperature distribution in the pair of electrodes can be suppressed, and decrease of the detection accuracy at the second detection portion can be suppressed.

Next, in the gas sensor element of the present disclosure, the element protection portion may include an inside protection portion which contacts the element body portion, and an outside protection portion which covers the inside protection portion.

The inside protection portion has a greater porosity than the outside protection portion. The outside protection portion contacts the element body portion at the rear side with respect to the inside protection portion.

The gas sensor element has a configuration in which the porosity of the inside protection portion is greater than the porosity of the outside protection portion. Accordingly, the moving amount of the gas between the porous portion and the inside protection portion can be suppressed from becoming too small.

Next, the gas sensor element of the present disclosure further comprises a specific protection portion formed in a portion higher than the second detection portion in the element protection portion in a height direction perpendicular to the second detection side face, wherein the interval dimension between the front end of the second detection portion and the rear end of the specific protection portion in the axial direction may be not less than 2.0 mm.

When the element protection portion is formed such that the front end of the second detection portion is separated from the rear end of the specific protection portion by a certain distance or greater in this manner, influence of the element protection portion on the supply of the measurement target gas to the second detection portion can be reduced. That is, in the gas sensor element, the amount of the measurement target gas supplied to the second detection portion can be suppressed from decreasing compared with that when the element protection portion is not provided, and the gas detection at the second detection portion is preferable, with the element protection portion provided.

Next, in the gas sensor element of the present disclosure, a preliminary protection layer having a smaller height than the second detection portion may be provided on the second detection side face and in a region between the second detection portion and the specific protection portion.

Since such a preliminary protection layer is provided, the element body portion (second detection side face) is protected, and at the same time, decrease in the amount of the measurement target gas supplied to the second detection portion can be suppressed.

The preliminary protection layer may be formed from the same material as that of the element protection portion, or may be formed from a material different from that of the element protection portion. For the preliminary protection layer, any material can be used as long as the material can protect the element body portion from breakage.

Next, another mode of the present disclosure is a gas sensor including: a gas sensor element configured to detect a first component and a second component in a measurement target gas; and a housing configured to hold the gas sensor element. The gas sensor element is any one of the gas sensor elements described above.

Similar to the gas sensor element described above, in such a gas sensor, the measurement target gas easily reaches the second detection portion, and thus, decrease of the detection accuracy at the second detection portion can be suppressed.

Next, another mode of the present disclosure is a method for producing a gas sensor element configured to detect a first component and a second component in a measurement target gas. The gas sensor element includes at least an element body portion, a first detection portion, a second detection portion, and an element protection portion, and is any one of the gas sensor elements described above. The method for producing the gas sensor element includes a first step, a second step, a third step, and a fourth step.

In the first step, a vanishing material, which vanishes due to heating, is applied so as to cover the second detection portion in an element member including the element body portion, the first detection portion, and the second detection portion, or the vanishing material is applied, at an unsintered element member which is to function as the element member after sintering, so as to cover a pre-sintering detection member which is to function as the second detection portion after sintering.

In the second step, after the first step, a pre-sintering protection material is applied which is to function as the element protection portion after sintering, so as to cover all of the second detection region and a region at the front side with respect to the second detection region, in the element member or the unsintered element member. In the third step, the pre-sintering protection material is sintered to form the element protection portion and cause the vanishing material to vanish. In the fourth step, the portion covering the second detection portion in the element protection portion generated through sintering of the pre-sintering protection material is removed.

This production method includes the first step, the third step, and the fourth step. Thus, when the pre-sintering protection material is applied in the second step, the pre-sintering protection material can be applied so as to cover all of the second detection region and the region at the front side with respect to the second detection region. That is, in production of the gas sensor element including the element protection portion that does not cover the second detection portion, the application work of the pre-sintering protection material does not require a special measure such as avoiding the second detection portion. Thus, increase of burden of work can be suppressed.

Similar to the gas sensor element described above, according to the gas sensor element obtained by this production method, the element protection portion alleviates thermal shock, and thus, occurrence of breakage of the gas sensor element can be suppressed. In addition, since the measurement target gas easily reaches the second detection portion, decrease of the detection accuracy at the second detection portion can be suppressed.

Next, another mode of the present disclosure is a method for producing a gas sensor element configured to detect a first component and a second component in a measurement target gas, and the method includes a protection portion liquid attaching step.

The gas sensor element includes at least an element body portion, a first detection portion, a second detection portion, and an element protection portion, and is any one of the gas sensor elements described above.

The protection portion liquid attaching step is a step of dipping the element body portion into a protection portion liquid which is to function as the element protection portion through sintering, thereby attaching the protection portion liquid to the element body portion. In the protection portion liquid attaching step, the protection portion liquid is attached to the element body portion by: dipping the porous portion into the protection portion liquid in a state where the porous portion of the first detection portion is at the lower side, the second detection portion is at the upper side, and the element body portion is oblique to the surface of the protection portion liquid; and lowering the element body portion to a position where the second detection portion is not dipped in the protection portion liquid.

Accordingly, without performing a step of providing carbon (sublimation material) so as to cover the second detection portion and a step of removing the element protection portion, it is possible to form the element protection portion that covers the porous region but that does not cover the second detection portion. Thus, according to the method for producing the gas sensor element, the steps can be simplified, and the complexity of production of the gas sensor element can be reduced.

Next, the method for producing the gas sensor element of the present disclosure may include a preliminary paste formation step when the gas sensor element includes a preliminary protection layer. The preliminary protection layer is a protection layer that is provided in a region, in the second detection side face, between the second detection portion and the specific protection portion, and that has a smaller height than the second detection portion. The preliminary paste formation step is a step performed before the protection portion liquid attaching step, and is a step of forming, at the element body portion, a preliminary paste which is to function as the preliminary protection layer after sintering.

Accordingly, the preliminary protection layer can be provided in addition to the element protection portion, and it is possible to suppress occurrence of breakage in the element body portion in the region between the second detection portion and the specific protection portion in the second detection side face. That is, by performing the preliminary paste formation step first, and then, performing the protection portion liquid attaching step, it is possible to produce the gas sensor element in which the element body portion (second detection side face) is protected, and at the same time, it is possible to suppress decrease in the amount of the measurement target gas supplied to the second detection portion.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Hereinafter, embodiments to which the present invention is applied will be described with reference to the drawings.

It is understood that the present invention is not limited to the following embodiments at all and various embodiments may be adopted without departing from the technical scope of the present invention.

1. FIRST EMBODIMENT 1-1. Overall Configuration

In a first embodiment, a multi-gas sensor 2 that is provided to an internal combustion engine of an automobile or the like is described.

Figure 1:
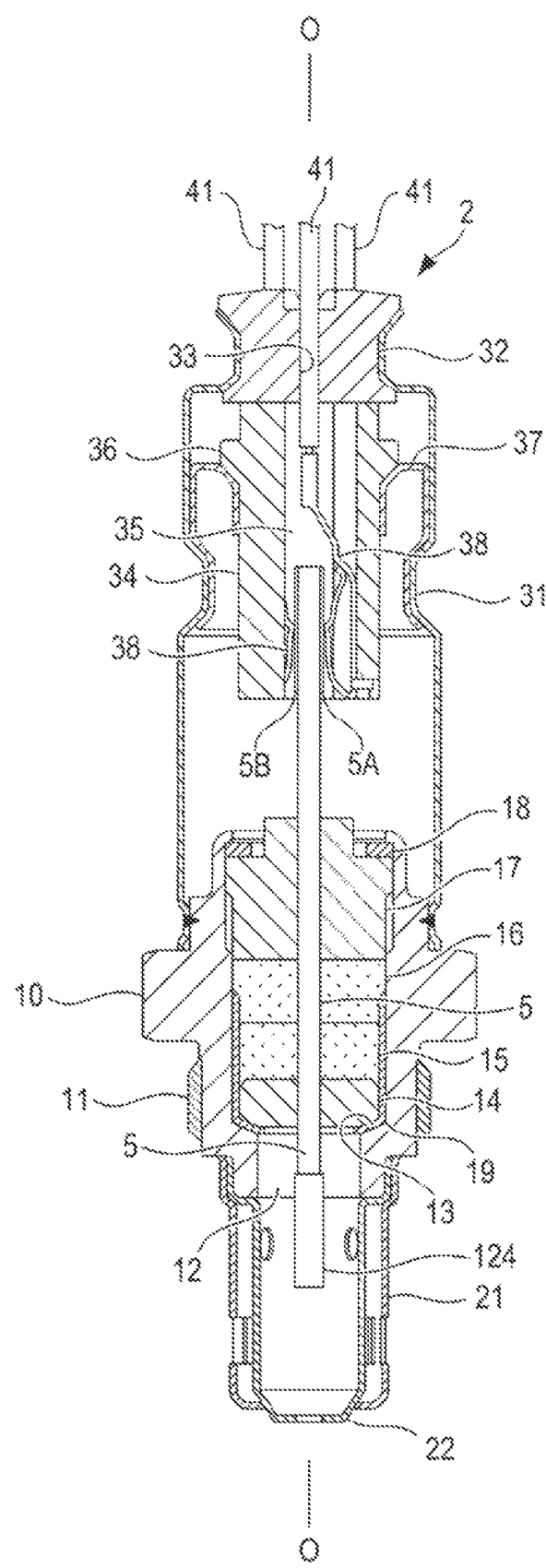
FIG. 1 is a cross-sectional view indicating the internal structure of a multi-gas sensor.

The multi-gas sensor 2 has a configuration as shown in FIG. 1, and is configured to detect an oxygen concentration, a NOx concentration, and an ammonia concentration ($NH_3$ concentration). The multi-gas sensor 2 forms a part of a multi-gas detection device 1.

The multi-gas detection device 1 is installed in a vehicle and is used in a urea SCR system which cleans nitrogen oxides contained in the exhaust gas exhausted from a diesel engine. More specifically, the multi-gas detection device 1 detects the concentrations of ammonia, nitrogen dioxide, and nitrogen oxides. Hereinafter, the vehicle having the multi-gas detection device 1 installed therein will be referred to as an own vehicle. Nitrogen dioxide and nitrogen oxides are also referred to as $NO_2$ and NOx, respectively. SCR is an acronym of Selective Catalytic Reduction.

Figure 2:
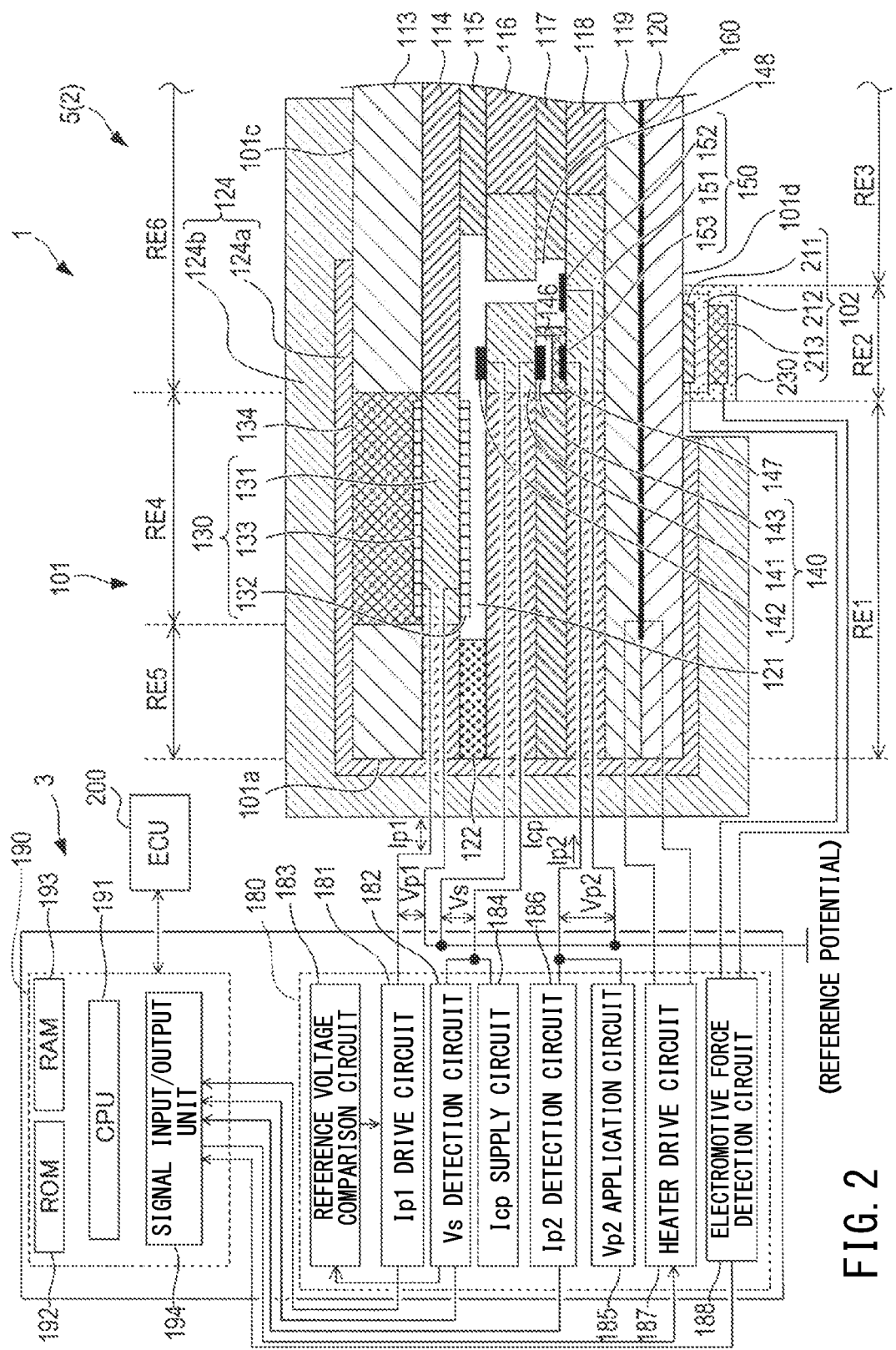
FIG. 2 is a view showing a schematic configuration of a multi-gas detection device 1.

The multi-gas detection device 1 includes the multi-gas sensor 2 and a controller 3 shown in FIG. 2.

The controller 3 is electrically connected to an electronic control unit 200 (also referred to as an ECU 200) installed in the own vehicle. The electronic control unit 200 receives data indicating the $NO_2$ concentration, the NOx concentration, and the ammonia concentration ($NH_3$ concentration) in the exhaust gas which are calculated by the controller 3, performs a control process regarding the operation state of the diesel engine on the basis of the received data, and performs a cleaning process for NOx accumulated in a catalyst.

1-2. Multi-Gas Sensor

As shown in FIG. 1, the multi-gas sensor 2 includes a sensor element portion 5, a metal shell 10, a separator 34, and connection terminals 38. In the following description, the side at which the sensor element portion 5 of the multi-gas sensor 2 is disposed (i.e., the lower side in FIG. 1) will be referred to as the front side, and the side at which the connection terminals 38 are disposed (i.e., the upper side in FIG. 1) will be referred to as the rear side.

The sensor element portion 5 has a plate shape extending in the direction of an axial line O. Electrode terminal portions 5A, 5B are disposed at the rear end of the sensor element portion 5. In FIG. 1, in order to simplify the drawing, only the electrode terminal portion 5A and the electrode terminal portion 5B are shown as the electrode terminal portions formed in the sensor element portion 5. However, in actuality, a plurality of electrode terminal portions are formed in accordance with the number of electrodes and the like of a NOx detection portion 101, a first ammonia detection portion 102, and a second ammonia detection portion 103 described later.

The metal shell 10 is a tubular-shaped member having an outer surface that has formed thereon a screw portion 11 for fixing the multi-gas sensor 2 to an exhaust pipe of the diesel engine. The metal shell 10 includes: a through hole 12 which penetrates in the direction of the axial line O; and a shelf portion 13 which protrudes radially inside of the through hole 12. The shelf portion 13 is formed as an inwardly-oriented tapered face that is inclined from radially outside of the through hole 12 toward the center thereof and toward the front side.

The metal shell 10 holds the sensor element portion 5 in a state where the front side of the sensor element portion 5 protrudes from the through hole 12 to the front side, and the rear side of the sensor element portion 5 protrudes to the rear side with respect to the through hole 12.

In the through hole 12 of the metal shell 10, a ceramic holder 14; talc rings 15, 16 as powder-charged layers; and a ceramic sleeve 17, which are tubular-shaped members that surround the periphery of the sensor element portion 5 in the radial direction, are stacked in this order from the front side to the rear side.

A crimp packing 18 is disposed between the ceramic sleeve 17 and the end portion at the rear side of the metal shell 10. A metal holder 19 is disposed between the ceramic holder 14 and the shelf portion 13 of the metal shell 10. The metal holder 19 accommodates the talc ring 15 and the ceramic holder 14. The metal holder 19 and the talc ring 15 are integrated with each other in an airtight manner as a result of the talc ring 15 filled with powder that is compressed. The end portion at the rear side of the metal shell 10 is crimped such that the ceramic sleeve 17 is pressed toward the front side through the crimp packing 18. In addition, since the talc ring 16 filled with powder is compressed in the metal shell 10, the airtightness between the inner peripheral surface of the metal shell 10 and the outer peripheral surface of the sensor element portion 5 is ensured.

An external protector 21 having a gas flow hole and an internal protector 22 having a gas flow hole are provided at an end portion at the front side of the metal shell 10. Each of the external protector 21 and the internal protector 22 is a tubular-shaped member that is formed from a metal material such as stainless steel and of which an end portion at the front side is closed. The internal protector 22 is welded to the metal shell 10 in a state of covering an end portion at the front side of the sensor element portion 5. The external protector 21 is welded to the metal shell 10 in a state of covering the internal protector 22.

An end portion at the front side of a sheath 31 formed in a tubular shape is welded and fixed to the outer periphery of an end portion at the rear side of the metal shell 10. Further, at an opening which is an end portion at the rear side of the sheath 31, a grommet 32 which closes this opening is disposed.

The grommet 32 has formed therein lead wire insertion holes 33 into each of which a lead wire 41 is inserted. The lead wires 41 are electrically connected to the electrode terminal portion 5A and the electrode terminal portion 5B of the sensor element portion 5.

The separator 34 is a member formed in a tubular shape and disposed at the rear side of the sensor element portion 5. A space formed in the separator 34 is an insertion hole 35 which penetrates in the direction of the axial line O. A flange portion 36 which protrudes to the radially outer side is formed on the outer surface of the separator 34.

In the insertion hole 35 of the separator 34, a rear end portion of the sensor element portion 5 is inserted, and the electrode terminal portions 5A, 5B are disposed in the separator 34.

Between the separator 34 and the sheath 31, a metal holding member 37 formed in a tubular shape is disposed. The holding member 37 is in contact with the flange portion 36 of the separator 34 and with the inner face of the sheath 31, thereby holding the separator 34 in a fixed state with respect to the sheath 31.

The connection terminals 38 are each a member disposed in the insertion hole 35 of the separator 34, and are conductive members which electrically connect the electrode terminal portion 5A and the electrode terminal portion 5B of the sensor element portion 5 to the lead wires 41 independently of each other. In FIG. 1, in order to simplify the drawing, only two connection terminals 38 are shown.

The sensor element portion 5 includes the NOx detection portion 101, the first ammonia detection portion 102, the second ammonia detection portion 103, and an element protection portion 124. The second ammonia detection portion 103 is not shown in FIG. 2, but shown in FIG. 3. The first ammonia detection portion 102 and the second ammonia detection portion 103 are disposed in parallel to each other at substantially the same position as a reference electrode 143 in the longitudinal direction of the NOx detection portion 101 (i.e., the right-left direction in FIG. 2), such that the positions of the first ammonia detection portion 102 and the second ammonia detection portion 103 are different from each other in the width direction (i.e., the depth direction in FIG. 2) of the NOx detection portion 101. Thus, in FIG. 2, of the first ammonia detection portion 102 and the second ammonia detection portion 103, only the first ammonia detection portion 102 is shown.

The NOx detection portion 101 is formed by serially stacking an insulation layer 113, a ceramic layer 114, an insulation layer 115, a ceramic layer 116, an insulation layer 117, a ceramic layer 118, an insulation layer 119, and an insulation layer 120. The insulation layers 113, 115, 117, 119, 120 and the ceramic layers 114, 116, 118 are each mainly formed from alumina.

The NOx detection portion 101 includes a first measurement chamber 121 formed between the ceramic layer 114 and the ceramic layer 116. The NOx detection portion 101 introduces the exhaust gas from outside into the first measurement chamber 121 through a diffusion resistor 122 disposed between the ceramic layer 114 and the ceramic layer 116 so as to be adjacent to the first measurement chamber 121. The diffusion resistor 122 is formed from a porous material such as alumina.

The NOx detection portion 101 includes a first pumping cell 130. The first pumping cell 130 includes a solid electrolyte layer 131 and pumping electrodes 132, 133.

The solid electrolyte layer 131 is mainly formed from zirconia having oxygen ion conductivity. A part of the ceramic layer 114 in a region that is in contact with the first measurement chamber 121 is removed, and the solid electrolyte layer 131 is filled (embedded) in place of the removed ceramic layer 114.

The pumping electrodes 132, 133 are each mainly formed from platinum. The pumping electrode 132 is disposed on a face, of the solid electrolyte layer 131, that is in contact with the first measurement chamber 121. The pumping electrode 133 is disposed on a face of the solid electrolyte layer 131 at the side opposite to the pumping electrode 132, with the solid electrolyte layer 131 interposed between the pumping electrode 133 and the pumping electrode 132. The insulation layer 113, in the region where the pumping electrode 133 is disposed and the vicinity thereof, is removed, and a porous body 134 is filled in place of the removed insulation layer 113. The porous body 134 allows communication of a gas (e.g., oxygen) between the pumping electrode 133 and the outside.

The NOx detection portion 101 includes an oxygen concentration detection cell 140. The oxygen concentration detection cell 140 includes a solid electrolyte layer 141, a detection electrode 142, and the reference electrode 143.

The solid electrolyte layer 141 is mainly formed from zirconia having oxygen ion conductivity. A part of the ceramic layer 116 in a region at the rear side (i.e., the right side in FIG. 2) with respect to the solid electrolyte layer 131 is removed, and the solid electrolyte layer 141 is filled (embedded) in place of the removed ceramic layer 116.

The detection electrode 142 and the reference electrode 143 are each mainly formed from platinum. The detection electrode 142 is disposed on a face, of the solid electrolyte layer 141, that is in contact with the first measurement chamber 121. The reference electrode 143 is disposed on a face of the solid electrolyte layer 141 at the side opposite to the detection electrode 142, with the solid electrolyte layer 141 interposed between the reference electrode 143 and the detection electrode 142.

The NOx detection portion 101 includes a reference oxygen chamber 146. The reference oxygen chamber 146 is a through hole formed by removing the insulation layer 117 from the region where the reference electrode 143 is disposed and the vicinity thereof.

The NOx detection portion 101 includes a second measurement chamber 148 at the downstream side of the first measurement chamber 121. The second measurement chamber 148 is formed so as to penetrate the solid electrolyte layer 141 and the insulation layer 117 at the rear side with respect to the detection electrode 142 and the reference electrode 143. The NOx detection portion 101 introduces the exhaust gas exhausted from the first measurement chamber 121 into the second measurement chamber 148.

The NOx detection portion 101 includes a second pumping cell 150. The second pumping cell 150 includes a solid electrolyte layer 151 and pumping electrodes 152, 153.

The solid electrolyte layer 151 is mainly formed from zirconia having oxygen ion conductivity. The ceramic layer 118, in the region that is in contact with the reference oxygen chamber 146 and the second measurement chamber 148, and the vicinity thereof, is removed, and the solid electrolyte layer 151 is filled (embedded) in place of the ceramic layer 118.

The pumping electrodes 152, 153 are each mainly formed from platinum. The pumping electrode 152 is disposed on a face, of the solid electrolyte layer 151, that is in contact with the second measurement chamber 148. The pumping electrode 153 is disposed on a face of the solid electrolyte layer 151, at the side opposite to the reference electrode 143 and with the reference oxygen chamber 146 interposed between the pumping electrode 153 and the reference electrode 143. A porous body 147 is disposed in the reference oxygen chamber 146 so as to cover the pumping electrode 153.

The NOx detection portion 101 includes a heater 160. The heater 160 is a heating resistor that is mainly formed from platinum and that generates heat by being energized. The heater 160 is disposed between the insulation layer 119 and the insulation layer 120.

The first ammonia detection portion 102 is formed on the outer surface of the NOx detection portion 101, more specifically, on the insulation layer 120. The first ammonia detection portion 102 is disposed at the same position in the direction of the axial line O (i.e., the right-left direction in FIG. 2) as the reference electrode 143 in the NOx detection portion 101.

Figure 3:
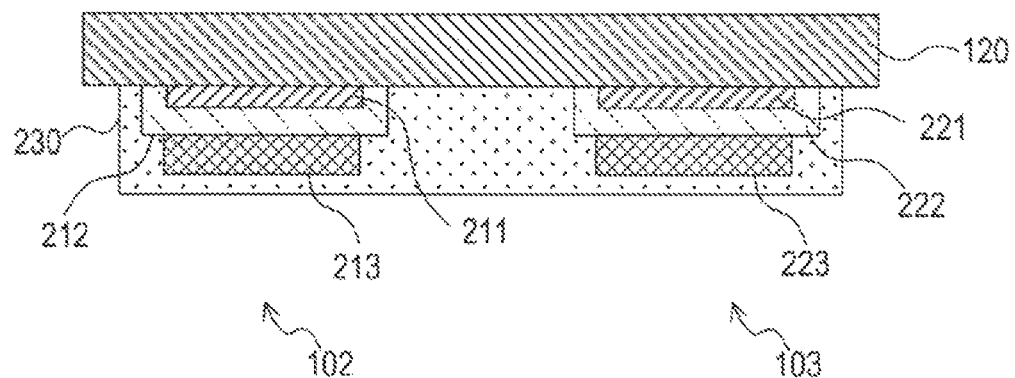
FIG. 3 is a cross-sectional view showing the structure of a first ammonia detection portion and a second ammonia detection portion.

The first ammonia detection portion 102 includes: a first reference electrode 211 formed on the insulation layer 120; a first solid electrolyte body 212 which covers the surface and the side face of the first reference electrode 211; and a first detection electrode 213 formed on the surface of the first solid electrolyte body 212. Similarly, as shown in FIG. 3, the second ammonia detection portion 103 includes: a second reference electrode 221 formed on the insulation layer 120; a second solid electrolyte body 222 which covers the surface and the side face of the second reference electrode 221; and a second detection electrode 223 formed on the surface of the second solid electrolyte body 222.

The first reference electrode 211 and the second reference electrode 221 are each mainly formed from platinum as an electrode material, and specifically, are formed from a material that contains Pt and zirconium oxide. The first solid electrolyte body 212 and the second solid electrolyte body 222 are each formed from an oxygen ion conductive material such as yttria-stabilized zirconia. The first detection electrode 213 and the second detection electrode 223 are each mainly formed from gold as an electrode material, and specifically, are formed from a material that contains Au and zirconium oxide. The electrode materials of the first detection electrode 213 and the second detection electrode 223 are selected such that the ratio between the sensitivity to ammonia and the sensitivity to $NO_2$ is different between the first ammonia detection portion 102 and the second ammonia detection portion 103.

The first ammonia detection portion 102 and the second ammonia detection portion 103 are integrally covered by a protection layer 230 in which a porous material is used. The protection layer 230 prevents poisonous substances from attaching to the first detection electrode 213 and the second detection electrode 223, and adjusts the diffusion speed of ammonia that flows from outside into the first ammonia detection portion 102 and the second ammonia detection portion 103. Thus, the first ammonia detection portion 102 and the second ammonia detection portion 103 function as a mixed potential-type sensing portion.

1-3. Element Protection Portion

Figure 4:
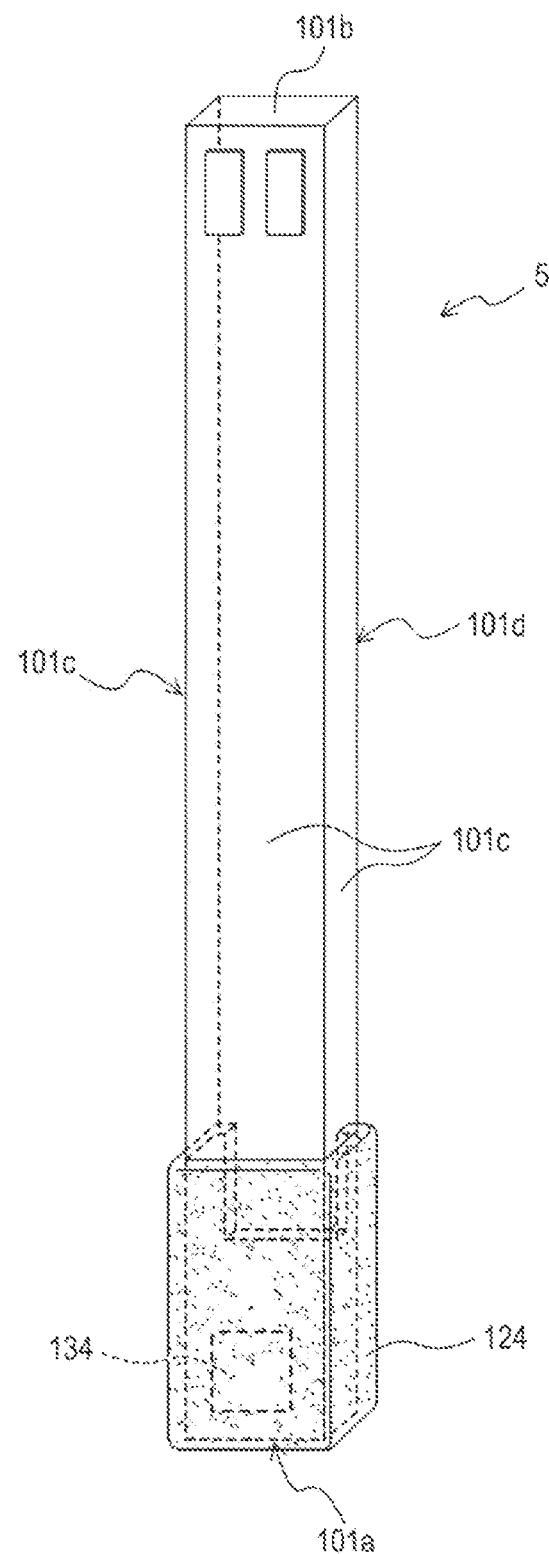
FIG. 4 is a perspective view of the external appearance of a sensor element portion.

As shown in FIG. 2 and FIG. 4, the sensor element portion 5 includes the element protection portion 124 which covers a front side region of the NOx detection portion 101.

The element protection portion 124 has a porous structure, and is configured to allow gas to pass therethrough.

The element protection portion 124 is formed so as to cover at least the porous body 134 in the NOx detection portion 101. The element protection portion 124 also covers the diffusion resistor 122 in the NOx detection portion 101.

The NOx detection portion 101 has, as outer surfaces thereof, a front end face 101a, a rear end face 101b, three normal side faces 101c, and one ammonia-detection side face 101d. The three normal side faces 101c are a normal side face 101c at which the porous body 134 is exposed and two normal side faces 101c continued from both sides thereof. On the ammonia-detection side face 101d, the first ammonia detection portion 102 and the second ammonia detection portion 103 are formed.

In the region along the axial direction of the NOx detection portion 101, the formation region of the first ammonia detection portion 102 (the second ammonia detection portion 103) (specifically, the protection layer 230) is defined as a second detection region RE2; the region at the front side with respect to the second detection region RE2 is defined as a first detection region RE1; and the region at the rear side with respect to the second detection region RE2 is defined as a third detection region RE3. The formation region of the porous body 134 is defined as a fourth detection region RE4; the region at the front side with respect to the fourth detection region RE4 is defined as a fifth detection region RE5; and the region at the rear side with respect to the fourth detection region RE4 is defined as a sixth detection region RE6. Here, in the axial direction, the front end of the second detection region RE2 is positioned to the front side with respect to the rear end of the fourth detection region RE4, and a part of the second detection region RE2 and a part of the fourth detection region RE4 overlap each other.

The porous body 134 is formed, at the plurality of side faces (three normal side faces 101c and one ammonia-detection side face 101d), in a front end region of two regions obtained by bisecting the NOx detection portion 101 in the axial direction. The first detection region RE1 consists of the entirety of the front end face 101a and parts of the side faces (parts of three normal side faces 101c and a part of one ammonia-detection side face 101d) of the NOx detection portion 101.

At the three normal side faces 101c, the element protection portion 124 is formed so as to cover at least the fourth detection region RE4 and the fifth detection region RE5. Further, at the three normal side faces 101c, the element protection portion 124 is configured to cover a part of the sixth detection region RE6. Specifically, the element protection portion 124 is formed so as to cover at least the formation region of the second pumping cell 150. Here, since the element protection portion 124 covers the fourth detection region RE4 and at least a part of the sixth detection region RE6, the boundary between the porous body 134 and the insulation layer 113 is also covered by the element protection portion 124.

Figure 5:
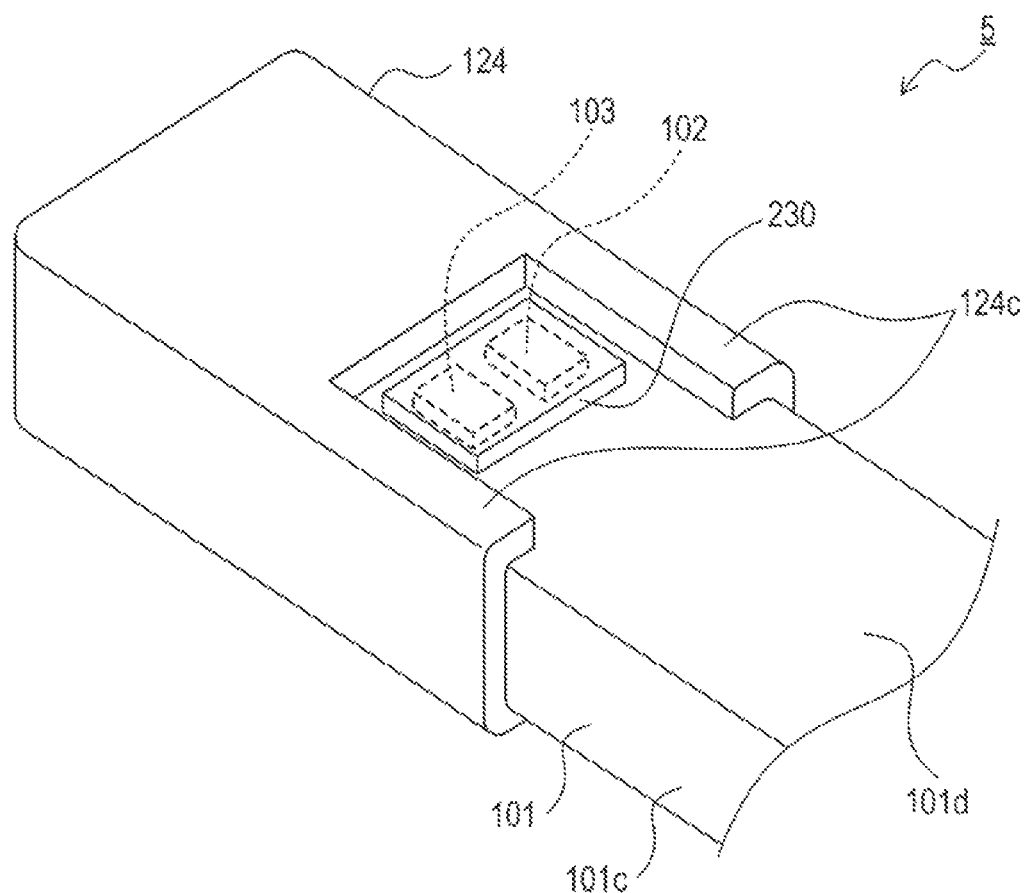
FIG. 5 is an enlarged perspective view of a portion in which the first ammonia detection portion and the second ammonia detection portion are provided, in a front end portion of the sensor element portion.

As shown in FIG. 2 and FIG. 5, at the ammonia-detection side face 101d, the element protection portion 124 is formed so as not to cover the first ammonia detection portion 102 (the second ammonia detection portion 103) (specifically, the protection layer 230), but to cover at least a part of the first detection region RE1. In addition, the element protection portion 124 has a communication portion 124c formed at the outer side, in the width direction, of the first ammonia detection portion 102 and the second ammonia detection portion 103. The communication portion 124c is a portion, of the element protection portion 124, that is formed on the ammonia-detection side face 101d, and is formed in a region, in the ammonia-detection side face 101d, excluding the first ammonia detection portion 102 and the second ammonia detection portion 103. The communication portion 124c is provided in a form that it communicates with a portion formed, at the normal side faces 101c, of the element protection portion 124. Since the element protection portion 124 has the communication portion 124c, detachment of the element protection portion 124 from the normal side faces 101c and the ammonia-detection side face 101d can be reduced.

That is, the sensor element portion 5 includes the element protection portion 124 that is formed so as to cover the porous body 134 (the porous portion of the NOx detection portion 101) without covering the first ammonia detection portion 102 and the second ammonia detection portion 103. Accordingly, the exhaust gas (measurement target gas) that is to reach the first ammonia detection portion 102 and the second ammonia detection portion 103 is not blocked by the element protection portion 124.

As shown in FIG. 2, the element protection portion 124 includes: an inside protection portion 124a that is in contact with the NOx detection portion 101; and an outside protection portion 124b that covers the inside protection portion 124a.

The inside protection portion 124a is formed by use of alumina, and has a porous structure of which porosity is 70%. The outside protection portion 124b is formed by use of alumina, and has a porous structure of which porosity is 46%. That is, the inside protection portion 124a has a porous structure that has a greater porosity than the outside protection portion 124b.

At the three normal side faces 101c, the outside protection portion 124b is in contact with the NOx detection portion 101 at the rear side with respect to the inside protection portion 124a.

1-4. Ammonia Detection Portion and Heater Portion

The NOx detection portion 101 includes the heater 160 as described above.

The heater 160 heats the first pumping cell 130, the oxygen concentration detection cell 140, the second pumping cell 150, the first ammonia detection portion 102, and the second ammonia detection portion 103.

Figure 6:
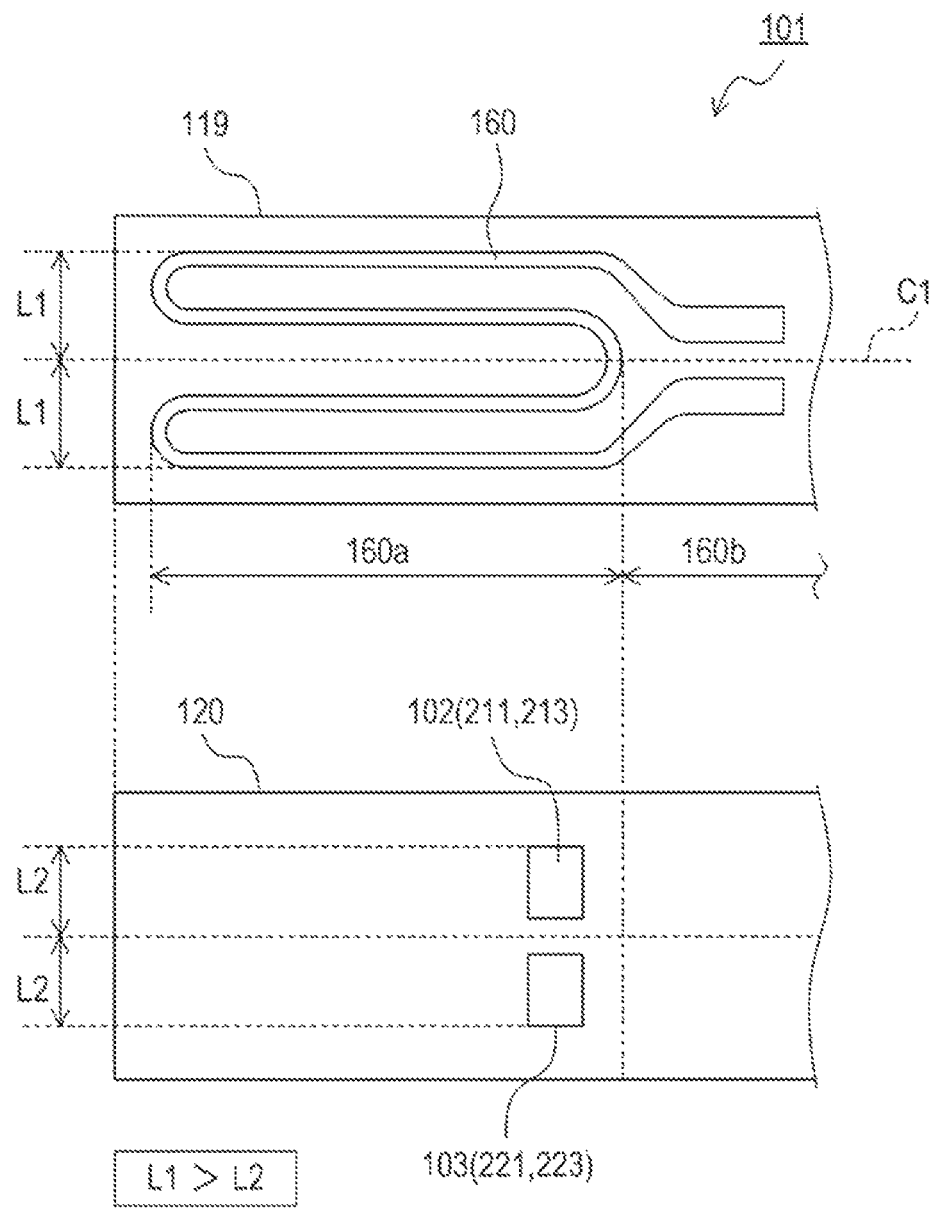
FIG. 6 is a schematic view for describing relative positions between a heat generation portion of a heater and a pair of electrodes in an ammonia detection portion.

As shown in FIG. 6, the heater 160 includes a heat generation portion 160a and a pair of heater lead portions 160b. The heat generation portion 160a is formed by use of a heating resistor that generates heat due to current application via the heater lead portions 160b.

The heat generation portion 160a is disposed so as to overlap at least one of "the formation region of the first pumping cell 130, the oxygen concentration detection cell 140, and the second pumping cell 150" and "the formation region of the first ammonia detection portion 102 and the second ammonia detection portion 103", in the axial direction.

When viewed in the width direction of the NOx detection portion 101, the heat generation portion 160a is disposed inside the arrangement regions which each extend by a heater width dimension L1 in the width direction (the up-down direction in FIG. 6) with respect to the center axis C1 of the NOx detection portion 101.

The first ammonia detection portion 102 includes a pair of detection electrodes (the first reference electrode 211, the first detection electrode 213). The second ammonia detection portion 103 includes a pair of detection electrodes (the second reference electrode 221, the second detection electrode 223).

When viewed in the width direction of the NOx detection portion 101, the pair of electrodes (the first reference electrode 211 and the first detection electrode 213) in the first ammonia detection portion 102, and the pair of electrodes (the second reference electrode 221 and the second detection electrode 223) in the second ammonia detection portion 103 are disposed inside the arrangement regions that each extend by a detection width dimension L2 in the width direction (the up-down direction in FIG. 6) with respect to the center axis C1 of the NOx detection portion 101.

The detection width dimension L2 is smaller than the heater width dimension L1. That is, the pair of electrodes in each of the first ammonia detection portion 102 and the second ammonia detection portion 103 is disposed inside the arrangement region of the heat generation portion 160a, in the width direction of the NOx detection portion 101.

Since the pair of electrodes of each of the first ammonia detection portion 102 and the second ammonia detection portion 103 is configured as described above, the entirety of the pair of electrodes easily receives heat from the heat generation portion 160a, compared with a case where the pair of electrodes is disposed in a region larger than the arrangement region of the heat generation portion 160a.

1-5. Method for Producing Sensor Element Portion

A method for producing the sensor element portion 5 is described.

First, a method for producing the NOx detection portion 101, the first ammonia detection portion 102, and the second ammonia detection portion 103, which are the base of the sensor element portion 5, is described.

First, a zirconia powder including a solid solution of a yttria stabilizer is caused to contain 20% by mass of an alumina powder, and the resultant mixture and a binder (polyvinyl butyral) are kneaded together to obtain a raw base material. This raw base material is used to produce an unsintered solid electrolyte sheet that is to function as a solid electrolyte layer and a solid electrolyte body. This unsintered solid electrolyte sheet is large enough to cut out a plurality of solid electrolyte layers and a plurality of solid electrolyte bodies therefrom.

In addition, a raw base material obtained by kneading an alumina powder and a binder (polyvinyl butyral) is used to produce an unsintered alumina sheet that is to function as an insulation layer or a ceramic layer after sintering. In the unsintered alumina sheet that is to function as a ceramic layer or an insulation layer that is designed to have a through hole (not shown) after sintering, the through hole is formed.

In an unsintered alumina sheet that is to function as a ceramic layer after sintering, an opening for disposing a solid electrolyte layer or the like therein is formed. The unsintered solid electrolyte sheet is embedded in the opening of the unsintered alumina sheet (or the raw base material is filled). Then, a conductive paste that contains platinum as a main component is printed into a predetermined pattern in a predetermined region on the sheet, and then is dried, thereby forming a conductor pattern that is to function as an electrode (the pumping electrode 132, 133, or the like) or a lead portion. In an unsintered alumina sheet that is designed to have a through hole, a conductive paste is applied to the inner wall surface of the through hole. Accordingly, an unsintered alumina sheet that is to function as a ceramic layer after sintering is obtained.

In an unsintered alumina sheet on which the heater 160 is to be formed, a conductive paste similar to that described above is printed into a predetermined pattern shape in a predetermined region, and then is dried, thereby forming a conductive pattern that is to function as the heat generation portion 160a and the heater lead portions 160b, and a conductor paste is applied to the inner wall surface of a through hole. To the face, of the unsintered alumina sheet, where the conductive pattern is printed, another unsintered alumina sheet is stacked, and the stacked sheets are pressure-bonded under reduced pressure, whereby an unsintered sheet for a heater is obtained.

Then, the unsintered alumina sheet that is to function as an insulation layer after sintering, the unsintered alumina sheet that is to function as a ceramic layer after sintering, the unsintered sheet for a heater, and the like are stacked in a predetermined order and pressure-bonded under reduced pressure, whereby an assembly is obtained.

At this time, a slurry obtained by mixing an alumina powder, a carbon powder as a pore forming agent, a binder composed of polyvinyl butyral, and a dispersing agent is filled into parts where the porous body 134, the diffusion resistor 122, and the like are to be formed. In addition, a slurry in which a carbon powder as a pore forming agent is mixed is filled into parts where the first measurement chamber 121, the second measurement chamber 148, and the like are to be formed.

Then, this assembly is cut by a known technique, whereby a plurality (e.g., 10) of unsintered laminated bodies are cut out. Then, each unsintered laminated body is degreased and subjected to a binder-removing process in the air atmosphere, and then, the resultant laminated body is sintered at 1500° C. for one hour, whereby the NOx detection portion 101 is obtained.

Then, the first ammonia detection portion 102 and the second ammonia detection portion 103 are formed at predetermined positions of the NOx detection portion 101. After the first ammonia detection portion 102 and the second ammonia detection portion 103 are formed, the protection layer 230 is formed so as to cover the first ammonia detection portion 102 and the second ammonia detection portion 103.

As the methods for producing the first ammonia detection portion 102, the second ammonia detection portion 103, and the protection layer 230, known production methods can be adopted. Thus, detailed description thereof is omitted here.

In this manner, the sensor element portion 5 at a stage before the element protection portion 124 is formed (in other words, an element member that includes the NOx detection portion 101, the first ammonia detection portion 102, the second ammonia detection portion 103, and the protection layer 230) is obtained.

Next, a method for forming the element protection portion 124 is described.

Figure 7A:
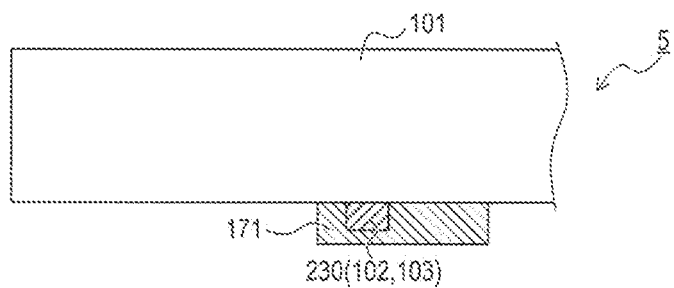
FIGS. 7A to 7D are stepwise views describing a first step to a fourth step in a method for forming an element protection portion.

First, in the first step, as shown in FIG. 7A, in the sensor element portion 5 at a stage before the element protection portion 124 is formed (an element member that includes the NOx detection portion 101, the first ammonia detection portion 102, the second ammonia detection portion 103, and the protection layer 230), a vanishing material 171 is applied so as to cover the protection layer 230 (the first ammonia detection portion 102, the second ammonia detection portion 103). The vanishing material 171 is a slurry that contains a carbon powder as a main component.

Figure 7B:
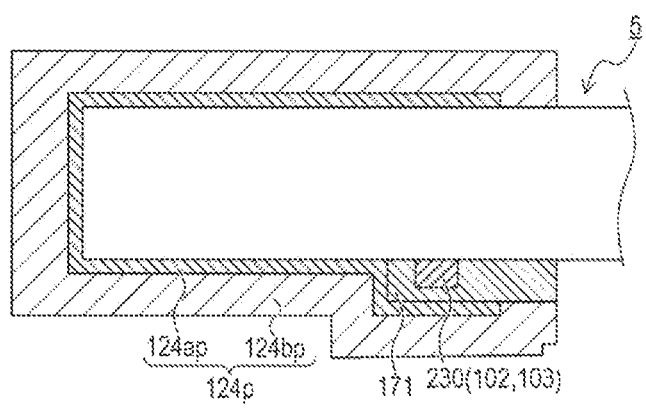

In the next second step, as shown in FIG. 7B, after the first step, a pre-sintering protection material 124p (in this specification, pre-sintering means "before sintering") is applied so as to cover, in the element member, all of the second detection region RE2 and the first detection region RE1 and a part of the third detection region RE3. The pre-sintering protection material 124p is a material that is to function as the element protection portion 124 after sintering, and is a slurry solution.

This slurry solution was prepared by: adding an organic solvent (e.g., ethanol, propylene glycol, butyl carbitol) to an alumina powder (average grain size<1 μm), an alumina fiber (average fiber length: 50 μm), a carbon powder (average grain size: 20 μm), and an alumina sol (external blend); stirring the mixture; and adjusting the mixture so as to have an appropriate viscosity. The contents of the respective components of the slurry solution are as follows, for example: 60 to 80% by volume of the alumina powder (average grain size<1 μm) and the alumina fiber (average fiber length: 50 μm) in total; 20 to 40% by volume of the carbon powder (average grain size: 20 μm); and 10% by weight of the alumina sol (external blend).

The average grain size of each powder that forms the slurry solution can be obtained by a laser diffraction scattering method, and the ceramic fiber length can be obtained by averaging the lengths of the respective ceramic fibers before being mixed into the slurry solution.

The pre-sintering protection material 124p includes: a pre-sintering inside material 124ap that is to function as the inside protection portion 124a after sintering; and a pre-sintering outside material 124bp that is to function as the outside protection portion 124b after sintering. By adjusting the content of each component in each of the pre-sintering inside material 124ap and the pre-sintering outside material 124bp, it is possible to control the porosities of the inside protection portion 124a and the outside protection portion 124b after sintering so as to have different values. For example, if the content of the carbon powder as a pore making material is adjusted, the porosity of the inside protection portion 124a can be controlled so as to be greater than the porosity of the outside protection portion 124b.

In the second step, first, the front end of the element member (the sensor element portion 5 at a stage before the element protection portion 124 is formed) is dipped into the slurry solution of the pre-sintering inside material 124ap, to form an inside application layer having a predetermined thickness (e.g., 100 μm) around the front end of the element member. Then, in order to cause excess organic solvent in the inside application layer to vanish, the element member provided with the inside application layer is disposed in a dryer set at 20 to 200° C. and is dried for several hours.

Next, the front end of the element member having the dried inside application layer formed thereon is dipped into the slurry solution of the pre-sintering outside material 124bp, to form an outside application layer having a predetermined thickness (e.g., 400 μm) around the front end of the element member. The thickness dimension can be controlled by, for example, adjusting the number of times of dipping into the slurry solution, the viscosity of the slurry solution, and the like. Then, in order to cause excess organic solvent in the outside application layer to vanish, the element member provided with the outside application layer is disposed in a dryer set at 20 to 200° C. and is dried for several hours.

Figure 7C:
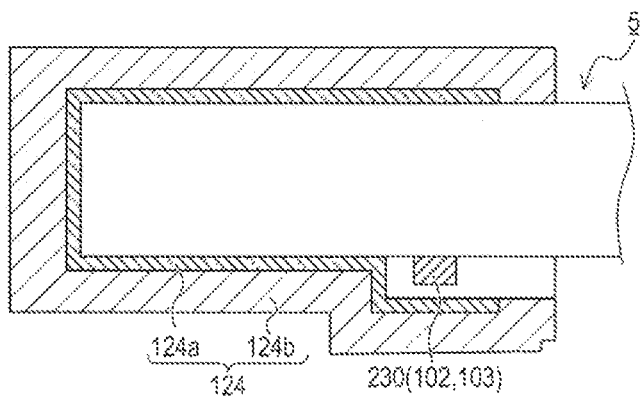

In the next third step, as shown in FIG. 7C, the element member provided with the inside application layer and the outside application layer is sintered in the air at 900 to 1100° C. for three hours, whereby the element protection portion 124 having the inside protection portion 124a and the outside protection portion 124b is obtained. During this sintering, the vanishing material 171 vanishes due to high temperature, whereby a space is provided between the protection layer 230 (the first ammonia detection portion 102, the second ammonia detection portion 103) and the inner face of the element protection portion 124.

Figure 7D:
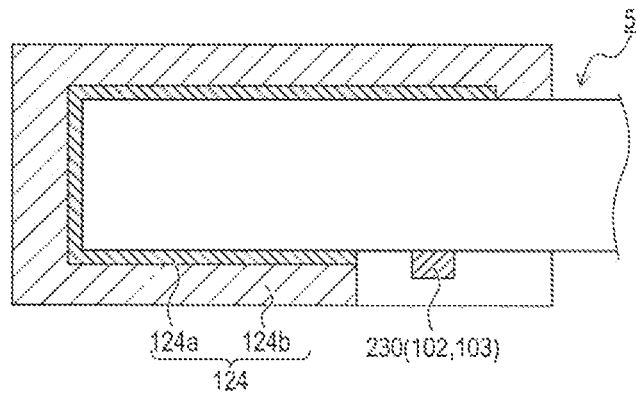

In the next fourth step, as shown in FIG. 7D, in the element protection portion 124 (the inside protection portion 124a, the outside protection portion 124b) generated through sintering of the pre-sintering protection material 124p (the pre-sintering inside material 124ap, the pre-sintering outside material 124bp), the portion that covers the protection layer 230 (the first ammonia detection portion 102, the second ammonia detection portion 103) is removed. The removing work of a part of the element protection portion 124 can be performed by use of, for example, a laser machining device, an ultrasonic cutter, or the like.

Accordingly, the sensor element portion 5 in which: the protection layer 230 (the first ammonia detection portion 102, the second ammonia detection portion 103) is exposed; and the element protection portion 124 is formed, is obtained.

Here, the inside application layer and the outside application layer are sintered at the same time after the inside application layer and the outside application layer have been formed, but the outside application layer may be sintered after the inside application layer has been sintered.

Then, the sensor element portion 5 produced by the above-described method is assembled to a housing (the metal shell 10, the sheath 31, and the like) according to a predetermined method, whereby the multi-gas sensor 2 can be produced.

1-6. Controller

As shown in FIG. 2, the controller 3 includes a control circuit 180 and a microcomputer 190.

The control circuit 180 is an analog circuit provided on a circuit board. The control circuit 180 includes an Ip1 drive circuit 181, a Vs detection circuit 182, a reference voltage comparison circuit 183, an Icp supply circuit 184, a Vp2 application circuit 185, an Ip2 detection circuit 186, a heater drive circuit 187, and an electromotive force detection circuit 188.

The pumping electrode 132, the detection electrode 142, and the pumping electrode 152 are connected to the reference potential. The pumping electrode 133 is connected to the Ip1 drive circuit 181. The reference electrode 143 is connected to the Vs detection circuit 182 and the Icp supply circuit 184. The pumping electrode 153 is connected to the Vp2 application circuit 185 and the Ip2 detection circuit 186. The heater 160 is connected to the heater drive circuit 187.

The Ip1 drive circuit 181 applies a voltage Vp1 between the pumping electrode 132 and the pumping electrode 133 to supply a first pumping current Ip1, and detects the supplied first pumping current Ip1.

The Vs detection circuit 182 detects a voltage Vs between the detection electrode 142 and the reference electrode 143, and outputs the detected result to the reference voltage comparison circuit 183.

The reference voltage comparison circuit 183 compares the reference voltage (e.g., 425 mV) with the output of the Vs detection circuit 182 (i.e., the voltage Vs), and outputs the comparison result to the Ip1 drive circuit 181. The Ip1 drive circuit 181 controls the direction of the flow of the first pumping current Ip1 and the magnitude of the first pumping current Ip1 such that the voltage Vs becomes equal to the reference voltage, and adjusts the oxygen concentration in the first measurement chamber 121 to such a predetermined value that would not cause decomposition of NOx.

The Icp supply circuit 184 causes a weak current Icp to flow between the detection electrode 142 and the reference electrode 143. Accordingly, oxygen is sent from the first measurement chamber 121 into the reference oxygen chamber 146 through the solid electrolyte layer 141. Accordingly, the reference oxygen chamber 146 is set to have a predetermined oxygen concentration serving as a reference.

The Vp2 application circuit 185 applies a constant voltage Vp2 (e.g., 450 mV) between the pumping electrode 152 and the pumping electrode 153. Accordingly, in the second measurement chamber 148, NOx is dissociated due to catalysis of the pumping electrodes 152, 153 forming the second pumping cell 150. Oxygen ions obtained through this dissociation move through the solid electrolyte layer 151 between the pumping electrode 152 and the pumping electrode 153, whereby a second pumping current Ip2 flows. The Ip2 detection circuit 186 detects the second pumping current Ip2.

The heater drive circuit 187 drives the heater 160 by applying a positive voltage for heater energization to one end of the heater 160 which is a heating resistor, and by applying a negative voltage for heater energization to the other end of the heater 160.

The electromotive force detection circuit 188 detects the electromotive force between the first reference electrode 211 and the first detection electrode 213 (hereinafter, first ammonia electromotive force), and the electromotive force between the second reference electrode 221 and the second detection electrode 223 (hereinafter, second ammonia electromotive force), and outputs signals indicating the detection results to the microcomputer 190.

The microcomputer 190 includes a CPU 191, a ROM 192, a RAM 193, and a signal input/output unit 194.

The CPU 191 performs a process for controlling the sensor element portion 5 on the basis of a program stored in the ROM 192. The signal input/output unit 194 is connected to the Ip1 drive circuit 181, the Vs detection circuit 182, the Ip2 detection circuit 186, the heater drive circuit 187, and the electromotive force detection circuit 188. The signal input/output unit 194 converts the voltage values of analog signals from the Ip1 drive circuit 181, the Vs detection circuit 182, the Ip2 detection circuit 186, and the electromotive force detection circuit 188 into digital data, and outputs the digital data to the CPU 191.

The CPU 191 outputs a drive signal to the heater drive circuit 187 via the signal input/output unit 194, thereby performing energization control, through pulse width modulation, of power to be supplied to the heater 160 such that the heater 160 has a target temperature. The energization control of the heater 160 can be realized by a known technique in which: the impedance of a cell (e.g., the oxygen concentration detection cell 140) forming the NOx detection portion 101 is detected; and the supply power amount is controlled such that the detected impedance has a target value.

The CPU 191 reads various types of data from the ROM 192, and performs various calculation processes on the basis of the value of the first pumping current Ip1, the value of the second pumping current Ip2, the value of the first ammonia electromotive force, and the value of the second ammonia electromotive force.

For the calculation processes performed by the CPU 191, known techniques can be used, and detailed description thereof is omitted here. For example, the CPU 191 first performs a calculation process for obtaining an oxygen concentration, a NOx concentration output, a first ammonia concentration output, and a second ammonia concentration output on the basis of the first pumping current Ip1, the second pumping current Ip2, the first ammonia electromotive force, and the second ammonia electromotive force. Then, the CPU 191 performs calculation using a predetermined correction formula by use of the oxygen concentration, the NOx concentration output, the first ammonia concentration output and the second ammonia concentration output, thereby obtaining the ammonia concentration, the $NO_2$ concentration and the NOx concentration in the exhaust gas.

The various functions of the microcomputer 190 are realized by the CPU executing a program stored in a non-transitory and substantive storage medium. In this example, the ROM corresponds to the non-transitory and substantive storage medium having the program stored therein. As a result of the program being executed, a method that corresponds to the program is performed. One or a plurality of microcomputers may form the controller 3. A part or the entirety of functions performed by the microcomputer may be configured as hardware such as one or a plurality of ICs.

The multi-gas detection device 1 having the controller 3 configured as described above calculates the concentrations of ammonia, $NO_2$, and NOx contained in the exhaust gas, by using the multi-gas sensor 2 which includes the NOx detection portion 101, the first ammonia detection portion 102, and the second ammonia detection portion 103.

1-7. Effect

As described above, the multi-gas sensor 2 of the present embodiment includes the sensor element portion 5 having the element protection portion 124.

The sensor element portion 5 includes the element protection portion 124 which is formed so as to cover the porous body 134 (the porous portion of the NOx detection portion 101) without covering the first ammonia detection portion 102 and the second ammonia detection portion 103. Thus, thermal shock can be alleviated, and occurrence of breakage of the sensor element portion 5 can be suppressed. In addition, the exhaust gas (measurement target gas) that is to reach the first ammonia detection portion 102 and the second ammonia detection portion 103 is not blocked by the element protection portion 124.

Therefore, in the sensor element portion 5, since the exhaust gas easily reaches the first ammonia detection portion 102 and the second ammonia detection portion 103, decrease of the detection accuracy at the first ammonia detection portion 102 and the second ammonia detection portion 103 can be suppressed.

Next, in the sensor element portion 5, the porosity of the inside protection portion 124a is greater than the porosity of the outside protection portion 124b. Thus, the sensor element portion 5 can suppress the moving amount of gas between the porous body 134 (the porous portion of the NOx detection portion 101) and the inside protection portion 124a from becoming too small.

Next, a pair of electrodes (the first reference electrode 211 and the first detection electrode 213; the second reference electrode 221 and the second detection electrode 223) in each of the first ammonia detection portion 102 and the second ammonia detection portion 103 is disposed inside the arrangement region of the heat generation portion 160a, in the width direction of the NOx detection portion 101.

When the pair of electrodes of each of the first ammonia detection portion 102 and the second ammonia detection portion 103 is configured as described above, the entirety of the pair of electrodes easily receives heat from the heat generation portion 160a, compared with a case where the pair of electrodes is disposed in a region larger than the arrangement region of the heat generation portion 160a.

Thus, in the sensor element portion 5, occurrence of unevenness of the temperature distribution in the pair of electrodes in each of the first ammonia detection portion 102 and the second ammonia detection portion 103 can be suppressed, and decrease of the detection accuracy at the first ammonia detection portion 102 and the second ammonia detection portion 103 can be suppressed.

As in the case of the sensor element portion 5, in the multi-gas sensor 2 including the sensor element portion 5, decrease of the detection accuracy at the first ammonia detection portion 102 and the second ammonia detection portion 103 can be suppressed.

Next, with respect to the method for producing the sensor element portion 5, since the method includes the first step, the third step, and the fourth step, when the pre-sintering protection material 124p (the pre-sintering inside material 124ap, the pre-sintering outside material 124bp) is to be applied in the second step, the pre-sintering protection material 124p can be applied so as to cover all of the second detection region RE2 and the first detection region RE1. That is, in production of the sensor element portion 5 including the element protection portion 124 that does not cover the first ammonia detection portion 102 and the second ammonia detection portion 103, the application work of the pre-sintering protection material 124p does not require a special measure such as avoiding the first ammonia detection portion 102 and the second ammonia detection portion 103. Therefore, as a method for applying the pre-sintering protection material 124p, a method of dipping an element member into a slurry solution (dip method) can be adopted. This method is a simple method of dipping the element member directly into a slurry solution. Thus, increase of burden of work in applying the pre-sintering protection material 124p can be suppressed.

1-8. Correspondence Relationship of Wordings

Here, the correspondence relationship of wordings is described.

The sensor element portion 5 corresponds to "gas sensor element", and the NOx detection portion 101 corresponds to "element body portion" and "first detection portion". The front end face 101a corresponds to "front end face", the rear end face 101b corresponds to "rear end face", the three normal side faces 101c and one ammonia-detection side face 101d correspond to "plurality of side faces", the ammonia-detection side face 101d corresponds to "second detection side face", each normal side face 101c corresponds to "normal side face", and the porous body 134 corresponds to "porous portion".

The first ammonia detection portion 102 and the second ammonia detection portion 103 correspond to one example of "second detection portion", the element protection portion 124 corresponds to one example of "element protection portion", the inside protection portion 124a corresponds to one example of "inside protection portion", and the outside protection portion 124b corresponds to one example of "outside protection portion". The vanishing material 171 corresponds to one example of "vanishing material", and the pre-sintering protection material 124p, the pre-sintering inside material 124ap, and the pre-sintering outside material 124bp correspond to one example of "pre-sintering protection material".

The second detection region RE2 corresponds to "second detection region", the first detection region RE1 corresponds to "region at front side with respect to second detection region", the heater 160 corresponds to "heater", the heat generation portion 160a corresponds to "heat generation portion", the first reference electrode 211 and the first detection electrode 213 correspond to "pair of detection electrodes", and the second reference electrode 221 and the second detection electrode 223 correspond to "pair of detection electrodes". The fourth detection region RE4 corresponds to "porous region".

The multi-gas sensor 2 corresponds to one example of "gas sensor", and the metal shell 10 corresponds to one example of "housing".

2. SECOND EMBODIMENT 2-1. Second Sensor Element Portion

As a second embodiment, a second sensor element portion 105 is described. The second sensor element portion 105 is different from the sensor element portion 5 of the first embodiment in the form of the element protection portion. Thus, the different portions are mainly described.

In the description below, in the second sensor element portion 105, the same components as those in the first embodiment are denoted by the same reference numerals used in first embodiment, and the details thereof are not described.

Figure 8:
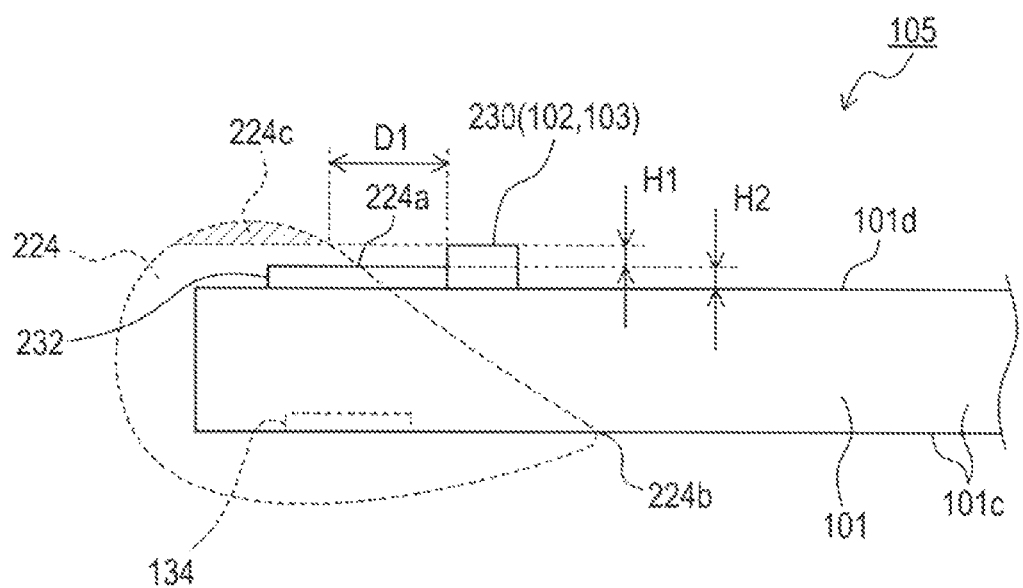
FIG. 8 is a view describing the configuration of a front end portion of a second sensor element portion according to a second embodiment.

As shown in FIG. 8, the second sensor element portion 105 includes the NOx detection portion 101, the first ammonia detection portion 102, the second ammonia detection portion 103, a second element protection portion 224, and a preliminary protection layer 232.

In FIG. 8, the front end portion of the second sensor element portion 105 is shown, and the rear end portion thereof is not shown. In FIG. 8, the second element protection portion 224 is indicated by a dotted line, and the portions, of the second sensor element portion 105, that are covered by the second element protection portion 224 (a part of the NOx detection portion 101, a part of the preliminary protection layer 232, etc.) are indicated by solid lines.

The second element protection portion 224 is formed from the same material as that of the element protection portion 124 of the first embodiment. The second element protection portion 224 is formed such that: the rear end (hereinafter, also referred to as a second rear end 224b) of the portion that covers the normal side face 101c where the porous body 134 is formed is positioned to the rear side of the NOx detection portion 101, with respect to the rear end of the portion (hereinafter, also referred to as a first rear end 224a) that covers the ammonia-detection side face 101d. In addition, the second element protection portion 224 is formed such that the first rear end 224a is positioned to the front side with respect to the protection layer 230, and the second rear end 224b is positioned to the rear side with respect to the protection layer 230.

Here, the portion (the region indicated by diagonal lines in FIG. 8), of the second element protection portion 224, that is higher than the protection layer 230 (the first ammonia detection portion 102, the second ammonia detection portion 103) in the direction perpendicular to the ammonia-detection side face 101d (height direction, i.e., the up-down direction in FIG. 8) is defined as a specific protection portion 224c. In the axial direction (the right-left direction in FIG. 8) of the second sensor element portion 105, an interval dimension D1 between the front end of the protection layer 230 (the first ammonia detection portion 102, the second ammonia detection portion 103) and the rear end of the specific protection portion 224c is 2.5 mm. That is, the second sensor element portion 105 is configured such that the interval dimension D1 is not less than 2.0 mm.

Figure 9:
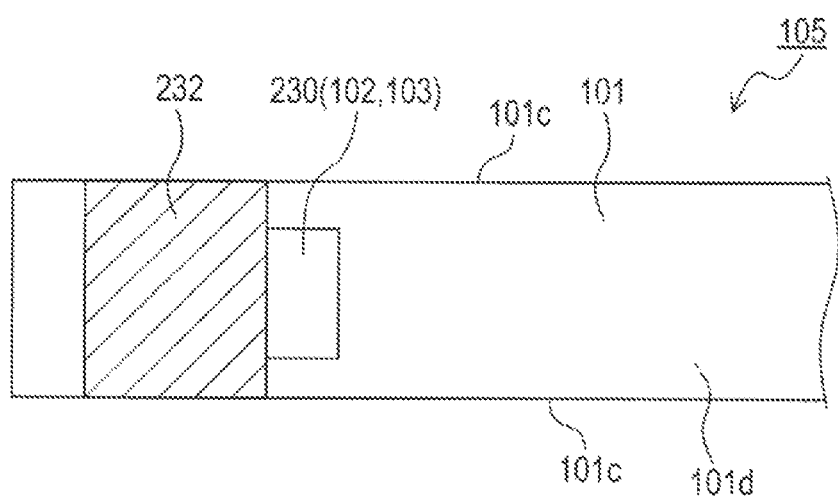
FIG. 9 is a view describing a position at which a preliminary protection layer and a protection layer (first ammonia detection portion, second ammonia detection portion) are formed in the second sensor element portion.

The preliminary protection layer 232 is formed from the same material as that of the second element protection portion 224. As shown in FIG. 8, the preliminary protection layer 232 is formed so as to be lower than the protection layer 230. A height dimension H2 of the preliminary protection layer 232 is 0.10 mm, and a height dimension H1 of the protection layer 230 is 0.15 mm. As shown in FIG. 9, the preliminary protection layer 232 is provided to the front side in the axial direction with respect to the protection layer 230 (the first ammonia detection portion 102, the second ammonia detection portion 103) in the ammonia-detection side face 101d of the NOx detection portion 101. The preliminary protection layer 232 has a front side region thereof covered by the second element protection portion 224.

That is, as shown in FIG. 8, the preliminary protection layer 232 is provided in a region, in the ammonia-detection side face 101d, between the first ammonia detection portion 102 (the second ammonia detection portion 103) and the specific protection portion 224c.

Next, a method for producing the second sensor element portion 105 is described.

First, the methods for producing the NOx detection portion 101, the first ammonia detection portion 102, the second ammonia detection portion 103, and the protection layer 230, which are the base of the second sensor element portion 105, are the same as those of the sensor element portion 5 of the first embodiment. Thus, description thereof is omitted.

After the second sensor element portion 105 at a stage before the second element protection portion 224 and the preliminary protection layer 232 are formed (in other words, an element member that includes the NOx detection portion 101, the first ammonia detection portion 102, the second ammonia detection portion 103, and the protection layer 230) is obtained, a preliminary paste formation step and a protection portion liquid attaching step are performed.

The preliminary paste formation step is a step performed before the protection portion liquid attaching step. The preliminary paste formation step is a step in which a preliminary paste 232a is applied to a predetermined region (see FIG. 9) in the ammonia-detection side face 101d of the NOx detection portion 101.

The preliminary paste 232a is a paste that is to function as the preliminary protection layer 232 through sintering. The preliminary paste 232a was prepared by: adding an organic solvent (e.g., ethanol, propylene glycol, butyl carbitol) to an alumina powder (average grain size<1 μm), an alumina fiber (average fiber length: 50 μm), a carbon powder (average grain size: 20 μm), and an alumina sol (external blend); stirring the mixture; and adjusting the mixture so as to have an appropriate viscosity. The contents of the respective components of the preliminary paste 232a are as follows, for example: 60 to 80% by volume of the alumina powder (average grain size<1 μm) and the alumina fiber (average fiber length: 50 μm) in total; 20 to 40% by volume of the carbon powder (average grain size: 20 μm); and 10% by weight of the alumina sol (external blend).

Then, in order to cause excess organic solvent in the preliminary paste 232a to vanish, the element member having the preliminary paste 232a applied thereto (the second sensor element portion 105 at a stage before the second element protection portion 224 is formed) is disposed in a dryer set at 20 to 200° C. and is dried for several hours.

The protection portion liquid attaching step is a step in which the second sensor element portion 105 at a stage before the second element protection portion 224 is formed is dipped into a protection portion liquid 225 to attach the protection portion liquid 225 to a predetermined region of the NOx detection portion 101.

The protection portion liquid 225 is a slurry solution that is to function as the second element protection portion 224 through sintering. This slurry solution was prepared by: adding an organic solvent (e.g., ethanol, propylene glycol, butyl carbitol) to an alumina powder (average grain size<1 μm), an alumina fiber (average fiber length: 50 μm), a carbon powder (average grain size: 20 μm), an alumina sol (external blend); stirring the mixture; and adjusting the mixture so as to have an appropriate viscosity. The contents of the respective components of the slurry solution are as follows, for example: 60 to 80% by volume of the alumina powder (average grain size<1 μm) and the alumina fiber (average fiber length: 50 μm) in total; 20 to 40% by volume of the carbon powder (average grain size: 20 μm); and 10% by weight of the alumina sol (external blend).

Figure 10:
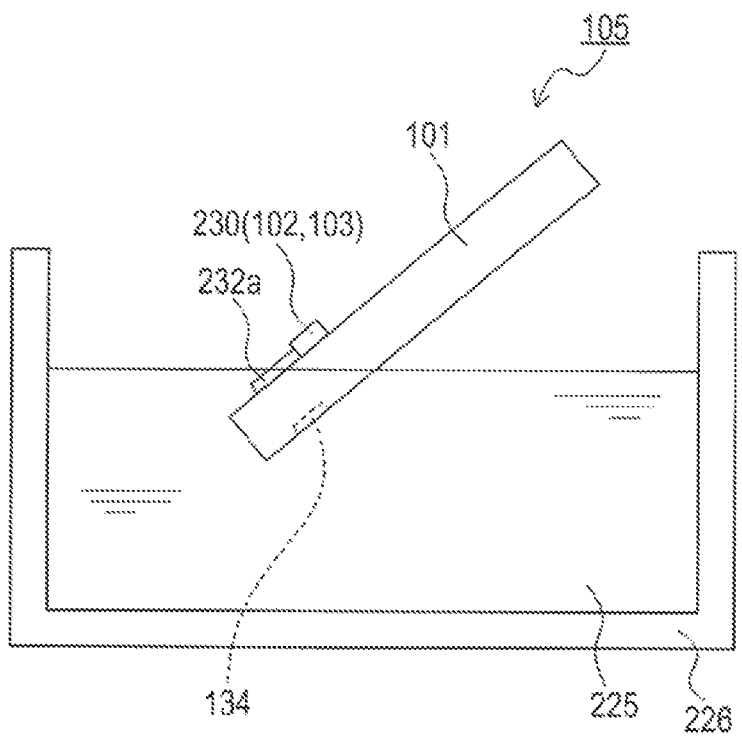
FIG. 10 is view describing a state where, in a protection portion liquid attaching step, a second sensor element portion at a stage before a second element protection portion is formed is dipped into a protection portion liquid stored in a container.

As shown in FIG. 10, in the protection portion liquid attaching step, the element member (the second sensor element portion 105 at a stage before the second element protection portion 224 is formed) is dipped into the protection portion liquid 225 stored in a container 226. At this time, the element member is dipped into the protection portion liquid 225 in a state where the porous body 134 in the NOx detection portion 101 is at the lower side, the first ammonia detection portion 102 (the second ammonia detection portion 103) is at the upper side, and the NOx detection portion 101 is oblique to the surface of the protection portion liquid 225. At this time, the element member is lowered to a position where: the porous body 134 is dipped in the protection portion liquid 225; and the first ammonia detection portion 102 (the second ammonia detection portion 103) is not dipped in the protection portion liquid 225. Accordingly, the protection portion liquid 225 can be attached to the element member (the second sensor element portion 105 at a stage before the second element protection portion 224 is formed).

Then, in order to cause excess organic solvent in the protection portion liquid 225 to vanish, the element member having the protection portion liquid 225 attached thereto is disposed in a dryer set at 20 to 200° C. and is dried for several hours.

Next, the element member having the preliminary paste and the protection portion liquid 225 attached thereto is sintered in the air at 900 to 1100° C. for three hours, whereby the second sensor element portion 105 in which the preliminary protection layer 232 and the second element protection portion 224 are formed is obtained.

Then, the second sensor element portion 105 thus produced is assembled to a housing (the metal shell 10, the sheath 31, and the like) according to a predetermined method, whereby the multi-gas sensor 2 can be produced.

2-2. Simulation Analysis Result and Measurement Result

Here, simulation analysis was performed regarding: in a case where a measurement target gas is supplied to the second sensor element portion 105, how the flow rate of the measurement target gas reaching the first ammonia detection portion 102 and the second ammonia detection portion 103 changes if the interval dimension D1 of the second sensor element portion 105 is changed. The analysis result is described.

It should be noted that the interval dimension D1 is the distance in the axial direction between the front end of the protection layer 230 (the first ammonia detection portion 102, the second ammonia detection portion 103) and the rear end of the specific protection portion 224c.

In the simulation analysis of the flow rate change, the flow rate, of the measurement target gas reaching the first ammonia detection portion 102 and the second ammonia detection portion 103, obtained when the measurement target gas was supplied to a sensor element portion not provided with the second element protection portion 224, was used as the reference value (100%), and the simulation analysis was performed. In the simulation analysis, a plurality of second sensor element portions 105 having different interval dimensions D1 were used. With respect to the flow rate analyzed with use of each second sensor element portion 105, the relative proportion to the reference value was calculated, and the calculation result was defined as gas-flow-rate proportion.

Figure 11:
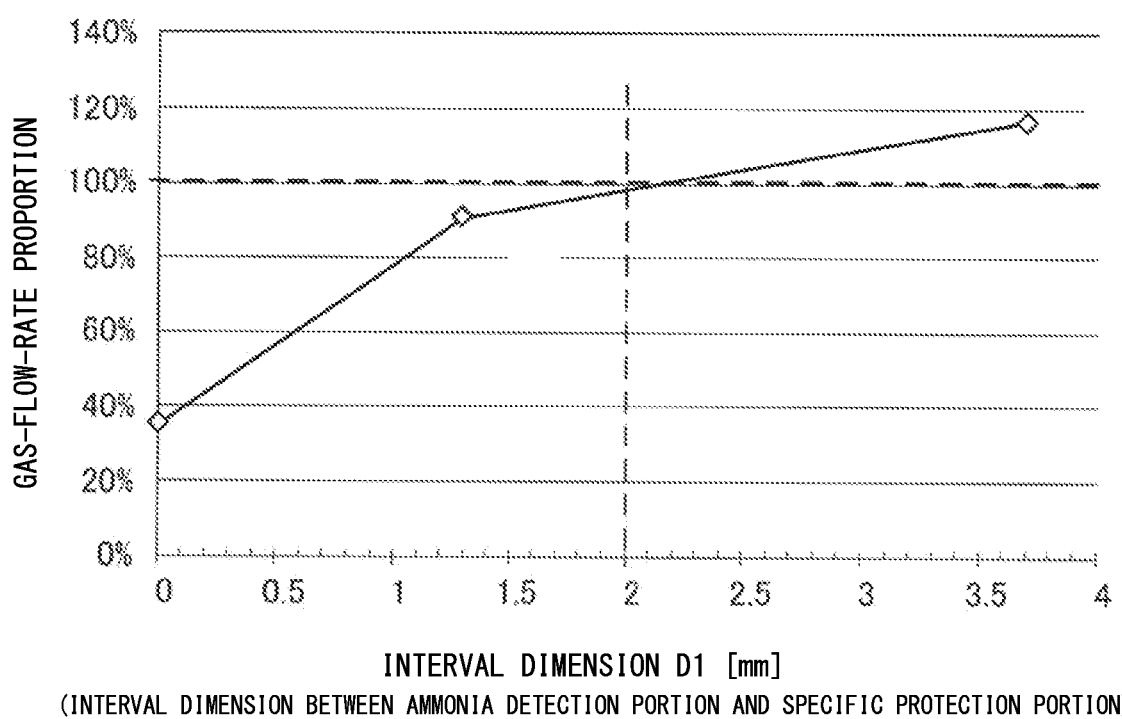
FIG. 11 is a result of simulation analysis regarding change of gas-flow-rate proportion according to interval dimension D1.

According to the simulation analysis result shown in FIG. 11, it is seen that: when the interval dimension D1 is not less than 1.5 mm, the gas-flow-rate proportion is not less than 90%; significant decrease in the amount of the measurement target gas supplied to the first ammonia detection portion 102 and the second ammonia detection portion 103 can be suppressed; and decrease of the gas detection accuracy can be suppressed. Further, it is seen that: when the interval dimension D1 is not less than 2.0 mm, the gas-flow-rate proportion becomes substantially 100%; the measurement target gas can be sufficiently supplied to the first ammonia detection portion 102 and the second ammonia detection portion 103; and the gas detection accuracy is preferable.

According to this simulation analysis result, when the second element protection portion 224 is formed such that the front end of the first ammonia detection portion 102 (the second ammonia detection portion 103) is separated from the rear end of the specific protection portion 224c by a certain distance or greater, influence of the second element protection portion 224 on the supply of the measurement target gas to the first ammonia detection portion 102 (the second ammonia detection portion 103) can be reduced. That is, in the second sensor element portion 105 that has an interval dimension D1 of not less than 2.0 mm, compared with a case where the element protection portion is not provided, decrease in the amount of the measurement target gas supplied to the first ammonia detection portion 102 (the second ammonia detection portion 103) is suppressed, and the gas detection at the first ammonia detection portion 102 (the second ammonia detection portion 103) is preferable, with the second element protection portion 224 provided.

Next, a measurement result is described in which the gas detection accuracy at the sensor element portion 5 of the first embodiment and the gas detection accuracy at the second sensor element portion 105 of the second embodiment are compared.

In this measurement, the detection signals, of the first ammonia detection portion 102 and the second ammonia detection portion 103, obtained when the same measurement target gas was supplied, were measured for each of the sensor element portion 5 and the second sensor element portion 105. Then, on the basis of the recorded result, it was evaluated what difference of the detection accuracy (magnitude of the detection signal) was caused by the difference of the shape of the element protection portion.

As for the difference of the shape of the element protection portion, the element protection portion 124 of the sensor element portion 5 is provided with the communication portion 124c (see FIG. 5) formed at the outer side, in the width direction, of the first ammonia detection portion 102 and the second ammonia detection portion 103. In contrast to this, the second element protection portion 224 of the second sensor element portion 105 is not provided with the portion formed at the outer side, in the width direction, of the first ammonia detection portion 102 and the second ammonia detection portion 103 (see FIG. 8).

In this measurement, as a comparison reference, the detection signal, of each of the first ammonia detection portion 102 and the second ammonia detection portion 103, obtained when a sensor element portion not provided with the element protection portion (in FIG. 12, indicated as "without element protection portion") was used, was used as the reference value (100%). The measurement result was calculated as a relative value (output change proportion) with respect to the reference value.

Figure 12:
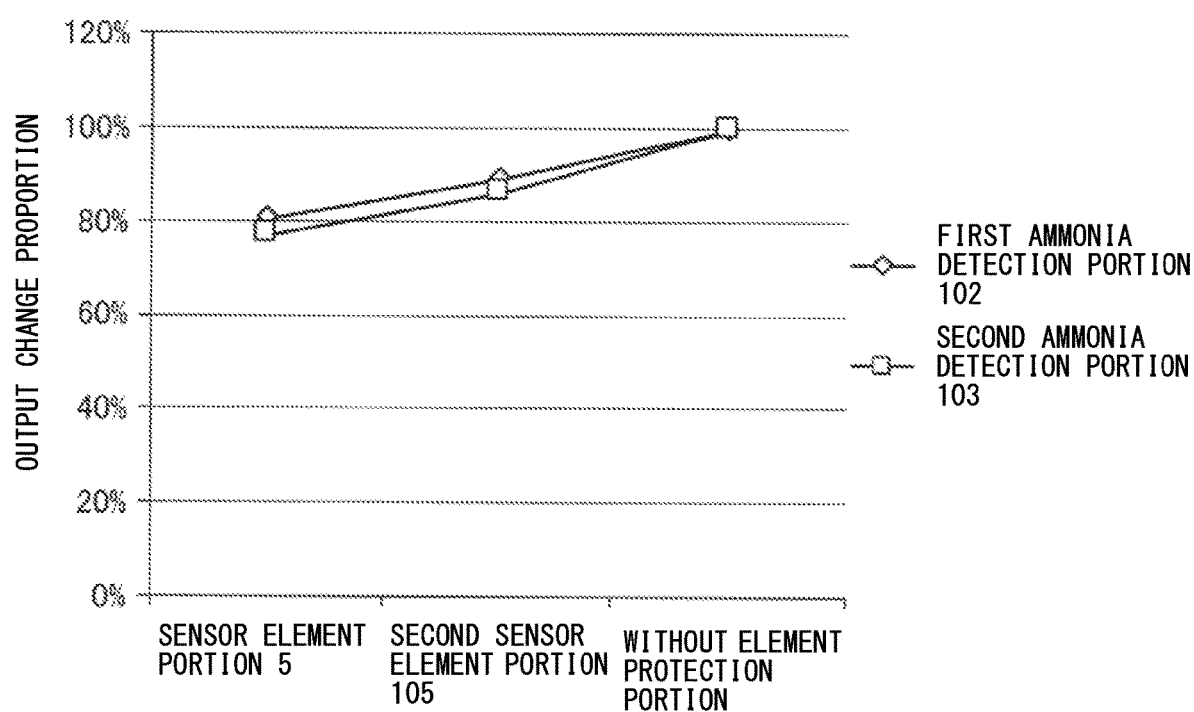
FIG. 12 is a measurement result in which gas detection accuracies of the sensor element portion of the first embodiment and the second sensor element portion of the second embodiment are compared with each other.

As shown in FIG. 12, for each of the second sensor element portion 105 and the sensor element portion 5, the output change proportion exceeds about 80%, and it is seen that, compared with a case where the element protection portion is not provided, significant decrease of the gas detection accuracy can be suppressed. In FIG. 12, the output change proportion of the sensor element portion not provided with the element protection portion is indicated as "without element protection portion".

In particular, in the second sensor element portion 105, the output change proportion of each of the first ammonia detection portion 102 and the second ammonia detection portion 103 is greater than that of the sensor element portion 5. Thus, it is seen that, compared with a configuration in which the communication portion 124c is provided as in the element protection portion 124 of the sensor element portion 5, the configuration in which the portion formed at the outer side, in the width direction, of the first ammonia detection portion 102 and the second ammonia detection portion 103 is not provided, as in the second element protection portion 224 of the second sensor element portion 105, is excellent in the detection accuracy of ammonia contained in the measurement target gas.

2-3. Effect

As described above, the second sensor element portion 105 of the second embodiment includes the second element protection portion 224. In the second sensor element portion 105, the interval dimension D1 in the axial direction between the front end of the first ammonia detection portion 102 (the second ammonia detection portion 103) and the rear end of the specific protection portion 224c is not less than 2.0 mm.

As shown in the simulation analysis result (FIG. 11) described above, when the second element protection portion 224 is formed such that the front end of the first ammonia detection portion 102 (the second ammonia detection portion 103) is separated from the rear end of the specific protection portion 224c by a certain distance or greater, influence of the second element protection portion 224 on the supply of the measurement target gas to the first ammonia detection portion 102 (the second ammonia detection portion 103) can be reduced. That is, in the second sensor element portion 105, compared with a case where the element protection portion is not provided, decrease in the amount of the measurement target gas supplied to the first ammonia detection portion 102 (the second ammonia detection portion 103) is suppressed, and the gas detection at the first ammonia detection portion 102 (the second ammonia detection portion 103) is preferable, with the second element protection portion 224 provided.

Next, the second sensor element portion 105 includes the preliminary protection layer 232 between the protection layer 230 (the first ammonia detection portion 102, the second ammonia detection portion 103) and the specific protection portion 224c, at the ammonia-detection side face 101d. The NOx detection portion 101 (the ammonia-detection side face 101d) is protected by the provision of the preliminary protection layer 232, and at the same time, decrease in the amount of the measurement target gas supplied to the protection layer 230 (the first ammonia detection portion 102, the second ammonia detection portion 103) can be suppressed.

Next, in the method for producing the second sensor element portion 105, the protection portion liquid attaching step is performed. Accordingly, without performing a step of providing carbon (sublimation material) so as to cover the first ammonia detection portion 102 (the second ammonia detection portion 103) and a step of removing the element protection portion, it is possible to form the second element protection portion 224 that covers the porous body 134 but that does not cover the first ammonia detection portion 102 (the second ammonia detection portion 103).

Thus, according to the method for producing the second sensor element portion 105, compared with the method for producing the sensor element portion 5 of the first embodiment, the steps can be simplified, and the complexity of production of the gas sensor element can be reduced.

Next, in the method for producing the second sensor element portion 105, the preliminary paste formation step is performed. Thus, in addition to the second element protection portion 224, the preliminary protection layer 232 can be provided. Accordingly, it is possible to suppress occurrence of breakage of the NOx detection portion 101 in the region between the protection layer 230 (the first ammonia detection portion 102, the second ammonia detection portion 103) and the specific protection portion 224c, in the ammonia-detection side face 101d of the NOx detection portion 101.

That is, by performing the preliminary paste formation step first, and then, performing the protection portion liquid attaching step, it is possible to produce a gas sensor element that can suppress decrease in the amount of the measurement target gas supplied to the protection layer 230 (the first ammonia detection portion 102, the second ammonia detection portion 103) while protecting the NOx detection portion 101 (the ammonia-detection side face 101d).

2-4. Correspondence Relationship of Wordings

Here, the correspondence relationship of wordings is described.

The second sensor element portion 105 corresponds to one example of "gas sensor element", the second element protection portion 224 corresponds to one example of "element protection portion", the specific protection portion 224c corresponds to one example of "specific protection portion", the preliminary protection layer 232 corresponds to one example of "preliminary protection layer", and the protection portion liquid 225 corresponds to one example of "protection portion liquid".

3. OTHER EMBODIMENTS

While the embodiments of the present invention have been described above, the present invention is not limited to the above embodiments, and may be carried out in various modes without departing from the gist of the present invention.

For example, in the above embodiments, description has been given of a production method in which: the pre-sintering protection material 124p is applied to a sintered element member (an element member provided with the NOx detection portion 101, the first ammonia detection portion 102, the second ammonia detection portion 103, and the protection layer 230); and the pre-sintering protection material 124p is sintered, whereby the element protection portion 124 is formed. However, the present invention is not limited to this production method. Specifically, the pre-sintering protection material 124p may be applied to an element member before sintering and the unsintered element member and the pre-sintering protection material 124p may be sintered at the same time.

In the above embodiments, as the sensor element portion, the sensor element portion 5 having the second detection portion (the first ammonia detection portion 102 and the second ammonia detection portion 103) formed on the side face that is close to the heater 160 among the side faces of the NOx detection portion 101 has been described. However, the present invention is not limited thereto. Specifically, the second detection portion may be provided on any of the three normal side faces 101c of the NOx detection portion 101.

Further, in the sensor element portion 5 of the first embodiment, the dimension (interval dimension) of the gap portion in the axial direction between the protection layer 230 (the first ammonia detection portion 102, the second ammonia detection portion 103) and the element protection portion 124 may be not less than 2.0 mm.

Further, in the sensor element portion 5 of the first embodiment, the preliminary protection layer may be provided in the region, between the protection layer 230 (the first ammonia detection portion 102, the second ammonia detection portion 103) and the element protection portion 124, in the ammonia-detection side face 101d of the NOx detection portion 101.

The preliminary protection layer 232 may not necessarily be formed from the same material as that of the second element protection portion 224, and may be formed from a material different from that of the second element protection portion 224. For the preliminary protection layer 232, any material can be used as long as the material can protect the NOx detection portion 101 (element body portion) from breakage.

The various numerical values described above (grain size, content, % by volume, thickness dimension, and the like) are not limited to those described above, and may be any values that fall within the technical scope described in claims.

Next, the function of one component in the above-described embodiments may be shared by a plurality of components, or the functions of a plurality of components may be performed by one component. Moreover, a part of the configuration in the above-described embodiments may be omitted. Furthermore, addition, replacement, or the like of at least a part of the configuration in the above-described embodiments may be made with respect to the configuration of other above-described embodiments. It should be noted that all aspects included in the technical idea specified by the wordings of the claims are embodiments of the present disclosure.

The present disclosure can also be realized in various forms such as a system having the microcomputer 190 as a component, a program for causing a computer to function as the microcomputer 190, a non-transitory and substantive storage medium such as a semiconductor memory having the program stored therein, a concentration calculation method, and the like, other than the microcomputer 190 described above.

DESCRIPTION OF REFERENCE NUMERALS

1: multi-gas detection device; 2: multi-gas sensor; 5: sensor element portion; 10: metal shell; 101: NOx detection portion; 101a: front end face; 101b: rear end face; 101c: normal side face; 101d: ammonia-detection side face; 102: first ammonia detection portion; 103: second ammonia detection portion; 105: second sensor element portion; 122: diffusion resistor; 124: element protection portion; 124a: inside protection portion; 124ap: pre-sintering inside material; 124b: outside protection portion; 124bp: pre-sintering outside material; 124p: pre-sintering protection material; 130: first pumping cell; 134: porous body; 140: oxygen concentration detection cell; 150: second pumping cell; 160: heater; 160a: heat generation portion; 171: vanishing material; 211: first reference electrode; 212: first solid electrolyte body; 213: first detection electrode; 221: second reference electrode; 222: second solid electrolyte body; 223: second detection electrode; 224: second element protection portion; 224c: specific protection portion; 225: protection portion liquid; 230: protection layer; 232: preliminary protection layer; L1: heater width dimension; L2: detection width dimension; RE1: first detection region; RE2: second detection region.

The invention claimed is:

1. A gas sensor element configured to detect a first component and a second component in a measurement target gas, the gas sensor element comprising:
an element body portion extending in an axial direction and having a front end face formed at a front end in the axial direction, a rear end face formed at a rear end in the axial direction, and a plurality of side faces extending from the front end face to the rear end face;
a first detection portion configured to pump out or pump in the measurement target gas through a porous portion formed on at least one of the plurality of side faces, and configured to detect the first component;
a second detection portion provided at a rear side with respect to a front end of the porous portion, and configured to detect the second component; and
an element protection portion configured to cover at least the porous portion, wherein
the plurality of side faces include a second detection side face on which the second detection portion is provided, and normal side faces which are not the second detection side face,
the element body portion comprises a second detection region that contains the second detection portion and extends in the axial direction and a porous region that contains the porous portion and extends in the axial direction,
the element protection portion covers the porous region and a region at a front side with respect to the porous region on the normal side faces, and covers a part of a region at a front side with respect to the second detection portion except for the second detection portion on the second detection side face, and
the element protection portion extends into the second detection region in the axial direction.

2. The gas sensor element according to claim 1, wherein
the element body portion includes a heater configured to heat the first detection portion and the second detection portion,
the heater includes a heat generation portion disposed so as to overlap at least one of the second detection region and a first detection region formed adjacent to the second detection region in the axial direction,
the second detection portion includes a pair of detection electrodes, and
the pair of detection electrodes is disposed inside an arrangement region of the heat generation portion in a width direction of the element body portion.

3. The gas sensor element according to claim 1, wherein
the element protection portion includes an inside protection portion which contacts the element body portion, and an outside protection portion which covers the inside protection portion,
the inside protection portion has a greater porosity than the outside protection portion, and
the outside protection portion contacts the element body portion at a rear side with respect to the inside protection portion.

4. The gas sensor element according to claim 1, further comprising a specific protection portion formed in a portion higher than the second detection portion in the element protection portion in a height direction perpendicular to the second detection side face, wherein
an interval dimension between a front end of the second detection portion and a rear end of the specific protection portion in the axial direction is not less than 2.0 mm.

5. The gas sensor element according to claim 4, wherein
a preliminary protection layer having a smaller height than the second detection portion is provided on the second detection side face and in a region between the second detection portion and the specific protection portion.

6. A gas sensor comprising:
a gas sensor element configured to detect a first component and a second component in a measurement target gas; and
a housing configured to hold the gas sensor element, wherein the gas sensor element is the gas sensor element according to claim 1.

7. A method for producing a gas sensor element configured to detect a first component and a second component in a measurement target gas, said gas sensor element including at least an element body portion, a first detection portion, a second detection portion, and an element protection portion, the gas sensor element being according to claim 1,
the method comprising:
- a first step of applying a vanishing material, which vanishes due to heating, so as to cover the second detection portion in an element member including the element body portion, the first detection portion, and the second detection portion, or applying, at an unsintered element member which is to function as the element member after sintering, the vanishing material so as to cover a pre-sintering detection member which is to function as the second detection portion after sintering;
- a second step of applying, after the first step, a pre-sintering protection material which is to function as the element protection portion after sintering, so as to cover all of the second detection region and a region at a front side with respect to the second detection region, in the element member or the unsintered element member;
- a third step of sintering the pre-sintering protection material to form the element protection portion and cause the vanishing material to vanish; and
- a fourth step of removing a portion covering the second detection portion in the element protection portion generated through sintering of the pre-sintering protection material.

8. A method for producing a gas sensor element configured to detect a first component and a second component in a measurement target gas, said gas sensor element including at least an element body portion a first detection portion, a second detection portion, and an element protection portion, the gas sensor element being according to claim 1,
the method for producing the gas sensor element comprising
a protection portion liquid attaching step of dipping the element body portion into a protection portion liquid which is to function as the element protection portion through sintering, thereby attaching the protection portion liquid to the element body portion, wherein
in the protection portion liquid attaching step, the protection portion liquid is attached to the element body portion by: dipping the porous portion into the protection portion liquid in a state where the porous portion of the first detection portion is at a lower side, the second detection portion is at an upper side, and the element body portion is oblique to a surface of the protection portion liquid; and lowering the element body portion to a position where the second detection portion is not dipped in the protection portion liquid.

9. The method for producing the gas sensor element according to claim 8, wherein
the gas sensor element includes a preliminary protection layer having a smaller height than the second detection portion in a region between the second detection portion and the specific protection portion, and
the method comprises, as a step to be performed before the protection portion liquid attaching step, a preliminary paste formation step of forming, at the element body portion, a preliminary paste which is to function as the preliminary protection layer through sintering.

* * * * *